US009334229B2

(12) United States Patent
Boaz et al.

(10) Patent No.: US 9,334,229 B2
(45) Date of Patent: May 10, 2016

(54) HYDROXYTYROSOL DERIVATIVES, THEIR METHOD OF PREPARATION AND USE IN PERSONAL CARE

(71) Applicant: Eastman Chemical Company, Kingsport, TN (US)

(72) Inventors: Neil Warren Boaz, Kingsport, TN (US); Robert Joseph Maleski, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 14/070,746

(22) Filed: Nov. 4, 2013

(65) Prior Publication Data

US 2015/0126759 A1    May 7, 2015

(51) Int. Cl.
| | |
|---|---|
| *C07C 69/96* | (2006.01) |
| *A61K 8/37* | (2006.01) |
| *A61Q 19/08* | (2006.01) |
| *C07C 67/31* | (2006.01) |
| *C07C 69/732* | (2006.01) |
| *C07C 69/738* | (2006.01) |
| *A61Q 19/00* | (2006.01) |
| *C07C 69/28* | (2006.01) |
| *C07C 67/293* | (2006.01) |
| *C07C 68/02* | (2006.01) |

(52) U.S. Cl.
CPC . *C07C 69/96* (2013.01); *A61K 8/37* (2013.01); *A61Q 19/00* (2013.01); *A61Q 19/08* (2013.01); *C07C 67/293* (2013.01); *C07C 67/31* (2013.01); *C07C 68/02* (2013.01); *C07C 69/28* (2013.01); *C07C 69/732* (2013.01); *C07C 69/738* (2013.01)

(58) Field of Classification Search
None
See application file for complete search history.

(56) References Cited

U.S. PATENT DOCUMENTS

| | | |
|---|---|---|
| 8,134,020 B2 | 3/2012 | Bruno et al. |
| 2003/0225160 A1 | 12/2003 | Geerlings et al. |
| 2005/0154058 A1* | 7/2005 | Gonzalez et al. ............. 514/546 |
| 2012/0059056 A1 | 3/2012 | Boaz |
| 2012/0269745 A1 | 10/2012 | Burton et al. |

FOREIGN PATENT DOCUMENTS

| | | | |
|---|---|---|---|
| FR | 2 919 800 A1 | 2/2009 | |
| WO | WO 2008/110908 A8 * | 9/2008 | ............. C07C 69/96 |
| WO | WO 2011/036537 A1 | 3/2011 | |

OTHER PUBLICATIONS

Notification of Transmittal of the International Search Report and the Written Opinion of the International Searching Authority with Date of Mailing Jan. 26, 2015 for International Application No. PCT/US2014/061679.
Bernini, Roberta, et al.; Convenient Synthesis of Hydroxytyrosol and Its Lipophilic Derivatives from Tyrosol or Homovanillyl Alcohol; Journal of Agricultural and Food Chemistry; 2008, 56, pp. 8897-8904.
Grasso, Salvatore, et al.; "Hydroxytyrosol lipophilic analogues: Enzymatic synthesis, radical scavenging activity and DNA oxidative damage protection"; Bioorganic Chemistry, 35, (2007), pp. 137-152.
Piersanti, Giovanni, et al.; "An efficient, economical synthesis of hydroxytyrosol and its protected forms via Baeyer-Villiger oxidation"; Tetrahedron Letters, 52, (2011), pp. 4938-4940.
Torres De Pinedo, A., et al.; "Efficient lipase-catalyzed synthesis of new lipid antioxidants based on a catechol structure"; Tetrahedron, 61, (2005), pp. 7654-7660.
Trujillo, Mariana, et al.; "Lipophilic Hydroxtyrosyl Esters. Antioxidant Activity in Lipid Matrices and Biological Systems"; Journal of Agricultural and Food Chemistry, 54, (2006), pp. 3779-3785.

* cited by examiner

*Primary Examiner* — Yate K Cutliff
(74) *Attorney, Agent, or Firm* — Matthew W. Smith; Dennis V. Carmen

(57) ABSTRACT

Hydroxytyrosol derivative compositions, methods for their manufacture, and their use in personal care products are disclosed. Lipophilic hydroxytyrosol carbonate ester compound can be made by oxidizing a substituted hydroxybenzaldehyde compound with an oxidizing agent such as hydrogen peroxide under mild conditions. The process involves enzymatic esterification of 4-(2-hydroxyethyl)phenol to form the corresponding ester, the introduction of a formyl group ortho to the phenolic hydroxyl group of the ester to form a lipophilic formyltyrosol ester; oxidation of the lipophilic formyltyrosol ester with a peroxide compound to form a lipophilic hydroxytyrosol ester compound; and reaction of lipophilic hydroxytyrosol ester compound with carbonic acid ester derivatives to form a lipophilic hydroxytyrosol carbonic ester compound. These compounds are useful is a wide variety of personal care compositions as anti-aging compounds that are stable against oxidation.

15 Claims, No Drawings

HYDROXYTYROSOL DERIVATIVES, THEIR METHOD OF PREPARATION AND USE IN PERSONAL CARE

1. FIELD OF THE INVENTION

The invention relates to compositions containing a hydroxytyrosol derivative and to their method of preparation, and further to their use in personal care applications.

2. BACKGROUND OF THE INVENTION

A large number of anti-aging skin care ingredients are phenolic in nature. Many of these function as anti-oxidants or skin illuminating ingredients, and the free hydroxyl groups are key to the redox activity of these species. Unfortunately, many of these materials have physical properties that are not well-suited for use as cosmetic ingredients. For example, they tend to have minimal solubility in most cosmetic solvents (both oils and water) and can be unstable in a cosmetic formulation (particularly towards oxidation). Derivatization of the phenolic groups can stabilize these materials. However, these derivatives must be readily removable under physiological conditions to liberate the phenolic groups and afford the desired anti-aging activity.

One useful method for derivatization of hydroxyl or carboxyl-containing materials is to prepare esters of these materials. The usefulness of this approach often depends upon the ability of enzymes in the skin to hydrolyze these esters to liberate the parent active ingredient. This strategy is effective for the derivatization of many active ingredients containing aliphatic, alicyclic, or alkaryl alcohols, but esters derived from phenols are often refractive or only slowly reactive towards enzymatic hydrolysis. As described in US Patent Application 2012/0059056 A1, progress in this area has been greatly advanced by the surprising discovery that carbonate esters are easily hydrolyzed in the presence of skin enzymes.

Hydroxytyrosol is a highly active and naturally occurring antioxidant of much interest as a stabilizer and anti-aging ingredient in cosmetic formulations, but the three polar hydroxyl groups make its compatibility with typical lipophilic skin care vehicles very poor. Moreover, even if a suitable vehicle could be found, its ease of air oxidation is a further challenge that limits its use for these applications.

It is desirable to obtain an anti-aging compound that is stable to oxidation, can be hydrolyzed to revert to an active compound, and is soluble in lipophilic vehicles or carriers that are often used in personal care compositions. It would also be desirable to provide a practical synthesis of such a compound from commercially available starting materials with high yields and minimal formation of by-products. A desirable synthesis would be suitable for scale-up to kilogram or larger quantities.

3. SUMMARY OF THE INVENTION

There is now provided a process for the manufacture of a lipophilic hydroxytyrosol ester represented by Formula 6:

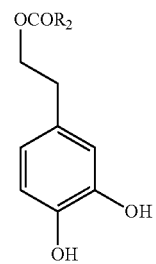

6 comprising oxidizing in a peroxide oxidation process a lipophilic formyltyrosol ester represented by Formula 5:

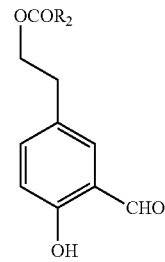

5 with a peroxide compound; wherein $R_2$ is a branched or straight chain, saturated or unsaturated, substituted or unsubstituted, $C_2$-$C_{24}$ aliphatic, alicyclic, or alkaryl group. The lipophilic hydroxytyrosol ester of Formula 6 can be further reacted in a carbonate process, said carbonate process comprising reacting said liphophilic hydroxytyrosol compound with a formate compound, a dicarbonate compound, or a mixture thereof, to obtain a hydroxytyrosol carbonate ester compound represented by Formula 2:

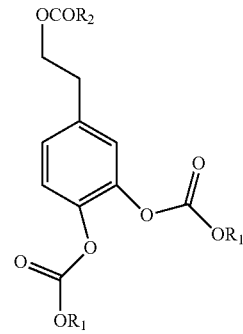

2

There is also provided a lipophilic hydroxytyrosol carbonate ester compound having a structure represented by the general Formula 2:

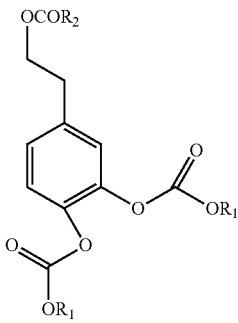

wherein $R_1$ is a saturated or unsaturated, branched or straight chain, substituted or unsubstituted, aliphatic, alicyclic, or alkaryl $C_1$-$C_{22}$ aliphatic, alicyclic, or alkaryl group; and wherein $R_2$ is a saturated or unsaturated, branched or straight chain, substituted or unsubstituted $C_2$-$C_{24}$ aliphatic, alicyclic, or alkaryl group.

There is further provided a composition for topical application to a keratinous surface, said composition comprising a lipophilic hydroxytyrosol carbonate ester compound of the general Formula 2:

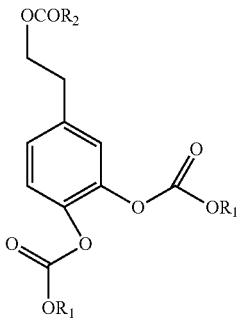

wherein $R_1$ is a saturated or unsaturated, branched or straight chain, substituted or unsubstituted, aliphatic, alicyclic, or alkaryl $C_1$-$C_{22}$ aliphatic, alicyclic, or alkaryl group; and wherein $R_2$ is a saturated or unsaturated, branched or straight chain, substituted or unsubstituted $C_2$-$C_{24}$ aliphatic, alicyclic, or alkaryl group.

4. DETAILED DESCRIPTION OF THE INVENTION

A dermatologically acceptable ingredient or composition means that the ingredient or composition is suitable for skin contact, preferably of humans, without undue toxicity, irritation, or allergic response. Those ingredients approved by any one of the US Food and Drug Administration, the European Commission, the European Medicines Agency, the European Food Safety Authority, the State Food and Drug Administration of the People's Republic of China, or Brazilian Health Ministry or its Sanitary Surveillance Agency for human skin contact are also deemed dermatologically acceptable.

Lipophilic hydroxytyrosol carbonate ester compounds and compositions of the invention provide good stability and solubility in typical cosmetic emollients. The lipophilic hydroxytyrosol carbonate ester compounds and compositions of the invention combine the stabilizing effect of the carbonate esters, their ease of hydrolysis in the presence of skin enzymes, and the solubilizing effect of the lipophilic hydroxyethyl ester in personal care formulations.

There is now provided a lipophilic hydroxytyrosol carbonate ester composition comprising a lipophilic hydroxytyrosol carbonate ester compound of the general Formula 2:

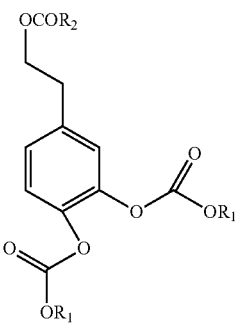

wherein:

$R_1$ comprises a branched or straight chain, saturated or unsaturated, substituted or unsubstituted, $C_1$-$C_{22}$ aliphatic, alicyclic, or alkaryl group; and $R_2$ comprises a branched or straight chain, saturated or unsaturated, substituted or unsubstituted, $C_2$-$C_{24}$ aliphatic, alicyclic, or alkaryl group. The saturated, unsaturated, and polyunsaturated groups, which may be represented by $R_1$ may be straight- or branched-chain aliphatic, alicyclic, or alkaryl hydrocarbon radicals containing up to about 22 carbon atoms and may be substituted, for example, with one to three groups selected from $C_1$-$C_6$-alkoxy, carboxyl, $C_1$-$C_{15}$ aminocarbonyl, $C_1$-$C_{15}$ amido, cyano, $C_2$-$C_{15}$-alkoxycarbonyl, $C_2$-$C_{15}$-alkoxycarbonyloxy, $C_2$-$C_{15}$-alkoxycarbonyloxyaryl, $C_2$-$C_{15}$-alkanoyloxy, hydroxy, aryl, substituted aryl, heteroaryl, substituted heteroaryl, thiol, thioether, and halogen. The terms "$C_1$-$C_6$-alkoxy", "$C_2$-$C_{15}$-alkoxycarbonyl", "$C_2$-$C_{15}$-alkoxycarbonyloxy", and "$C_2$-$C_6$-alkanoyloxy" are used to denote radicals corresponding to the structures —$OR_3$, —$CO_2R_4$, —$OCO_2R_4$, and —$OCOR_4$ respectively, wherein $R_3$ is $C_1$-$C_6$ straight or branched, substituted or unsubstituted aliphatic, alicyclic, or alkaryl and $R_4$ is $C_1$-$C_{14}$ straight or branched, substituted or unsubstituted aliphatic, alicyclic, or alkaryl. The terms "$C_1$-$C_{15}$-aminocarbonyl" and "$C_1$-$C_{15}$ amido" are used to denote radicals corresponding to the structures —$NHCOR_5$, —$CONHR_5$, respectively, wherein $R_5$ is $C_1$-$C_{15}$ straight or branched, substituted or un-substituted aliphatic, alicyclic, or alkaryl. The term "$C_2$-$C_{15}$-alkoxycarbonyloxyaryl" is used to denote radicals corresponding to the structures —Ar—$OCOOR_6$, wherein $R_6$ is a $C_1$-$C_{14}$ aliphatic, alicyclic, or alkaryl or substituted $C_1$-$C_{14}$ aliphatic, alicyclic, or alkaryl.

Desirably, $R_1$ is a $C_1$-$C_{12}$, or a $C_1$-$C_{10}$, or a $C_1$-$C_8$, or a $C_1$-$C_6$, or a $C_1$-$C_5$, or a $C_1$-$C_4$, or a $C_1$-$C_3$, or a $C_1$-$C_2$ branched or straight chain, saturated or unsaturated aliphatic, alicyclic, or alkaryl group, desirably an aliphatic group. For example, $R_1$ is a $C_1$-$C_8$, or a $C_1$-$C_6$, or a $C_1$-$C_5$, or a $C_1$-$C_4$, branched or straight chain, saturated, primary or secondary aliphatic, alicyclic, or alkaryl group.

$R_2$ is a branched or un-branched, saturated or un-saturated (which term includes poly-unsaturation) $C_2$-$C_{24}$ primary or secondary aliphatic, alicyclic, or alkaryl group. $R_2$ is optionally and desirably an unsubstituted aliphatic, alicyclic, or alkaryl group. For example, $R_2$ is a branched or un-branched, saturated or unsaturated (which term includes polyunsaturation) $C_6$-$C_{24}$, $C_8$-$C_{24}$, $C_{10}$-$C_{24}$, $C_{12}$-$C_{24}$, $C_{14}$-$C_{24}$ primary or secondary, branched or straight chain, saturated or unsaturated aliphatic, alicyclic, or alkaryl group, desirably an aliphatic group.

The $R_2$ can have more carbon atoms than the $R_1$ group. For example, the $R_2$ can have at least 2 more, or at least 3 more, or at least 4 more, or at least 5 more, or at least 6 more, or at least 7 more, or at least 8 more, or at least 9 more, or at least 10 more, or at least 11 more, or at least 12 more, or at least 13 more carbon atoms than are present in the $R_1$ group. For example, the $R_2$ can have from 2-20, or 2-18, or 2-16, or 2-14, or 2-12, or 2-10, or 2-8, or 2-6, or 2-4, or 3-20, or 3-18, or 3-16, or 3-14, or 3-12, or 3-10, or 3-8, or 3-6, or 3-4, or 4-20, or 4-18, or 4-16, or 4-14, or 4-12, or 4-10, or 4-8, or 4-6, or 5-20, or 5-18, or 5-16, or 5-14, or 5-12, or 5-10, or 5-8, or 5-6, or 6-20, or 6-18, or 6-16, or 6-14, or 6-12, or 6-10, or 6-8, or 7-20, or 7-18, or 7-16, or 7-14, or 7-12, or 7-10, or 7-8, or 8-20, or 8-18, or 8-16, or 8-14, or 8-12, or 8-10 more carbon atoms that are present in the $R_1$ group.

The particular selection of the type of $R_2$ group will depend upon the type of personal care formulation that is selected as the carrier. Although a lipophilic $R_2$ group can be selected that has good solubility in a wide range of personal care carrier compositions, the $R_2$ group selection can be further optimized to provide the most compatible combination with the particular type of carrier selected.

Further examples of $R_1$ and $R_2$ groups include the following combinations:

$R_2$=$C_6$-$C_{24}$ and $R_1$=$C_1$-$C_{12}$
$R_2$=$C_6$-$C_{24}$ and $R_1$=$C_1$-$C_{10}$
$R_2$=$C_6$-$C_{24}$ and $R_1$=$C_1$-$C_8$
$R_2$=$C_6$-$C_{24}$ and $R_1$=$C_1$-$C_6$
$R_2$=$C_6$-$C_{24}$ and $R_1$=$C_1$-$C_5$
$R_2$=$C_6$-$C_{24}$ and $R_1$=$C_1$-$C_4$
$R_2$=$C_6$-$C_{24}$ and $R_1$=$C_1$-$C_3$
$R_2$=$C_6$-$C_{24}$ and $R_1$=$C_1$-$C_2$
$R_2$=$C_8$-$C_{24}$ and $R_1$=$C_1$-$C_{12}$
$R_2$=$C_8$-$C_{24}$ and $R_1$=$C_1$-$C_{10}$
$R_2$=$C_8$-$C_{24}$ and $R_1$=$C_1$-$C_8$
$R_2$=$C_8$-$C_{24}$ and $R_1$=$C_1$-$C_6$
$R_2$=$C_8$-$C_{24}$ and $R_1$=$C_1$-$C_5$
$R_2$=$C_8$-$C_{24}$ and $R_1$=$C_1$-$C_4$
$R_2$=$C_8$-$C_{24}$ and $R_1$=$C_1$-$C_3$
$R_2$=$C_8$-$C_{24}$ and $R_1$=$C_1$-$C_2$
$R_2$=$C_{10}$-$C_{24}$ and $R_1$=$C_1$-$C_{12}$
$R_2$=$C_{10}$-$C_{24}$ and $R_1$=$C_1$-$C_{10}$
$R_2$=$C_{10}$-$C_{24}$ and $R_1$=$C_1$-$C_8$
$R_2$=$C_{10}$-$C_{24}$ and $R_1$=$C_1$-$C_6$
$R_2$=$C_{10}$-$C_{24}$ and $R_1$=$C_1$-$C_5$
$R_2$=$C_{10}$-$C_{24}$ and $R_1$=$C_1$-$C_4$
$R_2$=$C_{10}$-$C_{24}$ and $R_1$=$C_1$-$C_3$
$R_2$=$C_{10}$-$C_{24}$ and $R_1$=$C_1$-$C_2$
$R_2$=$C_{12}$-$C_{24}$ and $R_1$=$C_1$-$C_{12}$
$R_2$=$C_{12}$-$C_{24}$ and $R_1$=$C_1$-$C_{10}$
$R_2$=$C_{12}$-$C_{24}$ and $R_1$=$C_1$-$C_8$
$R_2$=$C_{12}$-$C_{24}$ and $R_1$=$C_1$-$C_6$
$R_2$=$C_{12}$-$C_{24}$ and $R_1$=$C_1$-$C_5$
$R_2$=$C_{12}$-$C_{24}$ and $R_1$=$C_1$-$C_4$
$R_2$=$C_{12}$-$C_{24}$ and $R_1$=$C_1$-$C_3$
$R_2$=$C_{12}$-$C_{24}$ and $R_1$=$C_1$-$C_2$
$R_2$=$C_{14}$-$C_{24}$ and $R_1$=$C_1$-$C_{12}$
$R_2$=$C_{14}$-$C_{24}$ and $R_1$=$C_1$-$C_{10}$
$R_2$=$C_{14}$-$C_{24}$ and $R_1$=$C_1$-$C_8$
$R_2$=$C_{14}$-$C_{24}$ and $R_1$=$C_1$-$C_6$
$R_2$=$C_{14}$-$C_{24}$ and $R_1$=$C_1$-$C_5$
$R_2$=$C_{14}$-$C_{24}$ and $R_1$=$C_1$-$C_4$
$R_2$=$C_{14}$-$C_{24}$ and $R_1$=$C_1$-$C_3$
$R_2$=$C_{14}$-$C_{24}$ and $R_1$=$C_1$-$C_2$ In all cases, desirably $R_2$ is unsubstituted.

Desirably, $R_2$ is an aliphatic group or alicyclic group. The term "alicyclic group" refers to a cyclic aliphatic group that can contain 1 or more linking alkyl carbon atoms. Desirably, $R_2$ is an aliphatic group, or an alkyl group.

Desirably, $R_2$ has no more than 3 unsaturated sites, or no more than 2, or no more than 1, or alternatively is saturated.

The lipophilic hydroxytyrosol carbonate ester compounds of Formula 2 and compositions thereof can be made by reacting a lipophilic hydroxytyrosol ester or composition with a chloroformate, bromoformate, or dicarbonate to produce the lipophilic hydroxytyrosol carbonate ester compounds of Formula 2 and the compositions containing the compounds of Formula 2. The lipophilic hydroxytyrosol esters and compositions can be represented by the following Formula 6:

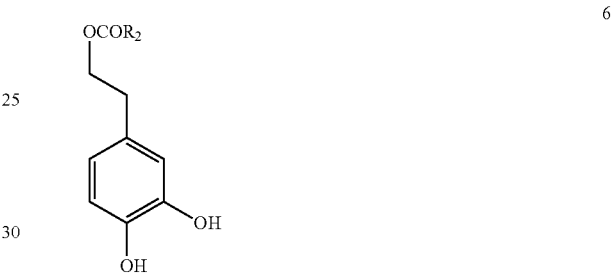

6 wherein $R_2$ is the $R_2$ group described above.

The process for converting the lipophilic hydroxytyrosol esters and compositions to lipophilic hydroxytyrosol carbonate ester compounds and compositions is referred to herein as the carbonate process. The carbonate process can be carried out with or without solvent or in an inert solvent chosen from cyclic or acyclic ether solvents, such as, diethyl ether, diisopropyl ether, tert-butyl methyl ether, or tetrahydrofuran; aromatic hydrocarbons, such as, benzene, toluene, or xylene; aliphatic, alicyclic, or alkaryl or alicyclic saturated or unsaturated hydrocarbons, such as, hexane, heptane, cyclohexane, or limonene; halogenated hydrocarbons, such as, dichloromethane, dichloroethane, dibromoethane, tetrachloroethylene, or chlorobenzene; polar aprotic solvents, such as, acetonitrile, dimethyl formamide, or dimethyl sulfoxide; aromatic N-heterocyclic solvents such as pyridine, picolines, or lutidines; ketones such as acetone, diethyl ketone, or methyl isobutyl ketone, or mixtures thereof. In one embodiment of the invention, no solvent is utilized. In another embodiment, dichloromethane, toluene, acetone, or mixtures thereof are utilized. In another embodiment, acetone is used as the solvent.

The carbonate process may be carried out at a temperature between about −100° C. and about 100° C. The carbonate process may be carried out at a temperature from about −100° C. and up to and including the boiling point of the solvent. Other temperature ranges include from about 0° C. and 60° C. and from about 0° C. to about 50° C.

The amount of chloroformate, bromoformate or dicarbonate may be between about 0.7 and about 20 equivalents for each hydroxyl group on the lipophilic hydroxytyrosol esters of Formula 6. In another embodiment, the amount of chloroformate, bromoformate or dicarbonate may be between about 1 and about 10 equivalents or between about 1 and about 2 equivalents for each hydroxyl group being derivatized on the lipophilic hydroxytyrosol esters of Formula 6.

The carbonate process can be run in the presence of an acid acceptor. Examples of acid acceptors include, but are not limited to, tertiary aliphatic, alicyclic, or alkarylamines with between 3 and 15 carbon atoms or substituted or un-substituted pyridines. The carbonate process may also be run in the presence of a catalyst. The catalyst may be a hypernucleophile such as N,N-dialiphatic, alicyclic, or alkarylaminopyridines or alkoxypyridines. The pressure for the reaction is not crucial and can range between about 1 torr to about 10 atm pressure. Another range is from about 200 torr to ambient pressure.

The lipophilic hydroxytyrosol carbonate ester compounds and compositions may be isolated using methods known to those of skill in the art, e.g., extraction, filtration, or crystallization. The lipophilic hydroxytyrosol carbonate ester compounds and compositions containing the lipophilic hydroxytyrosol carbonate ester compounds of Formula 2 may be purified if necessary using methods known to those of skill in the art, e.g., extraction, chromatography, distillation, or crystallization.

The lipophilic hydroxytyrosol esters, such as those represented by Formula 6, can be made by reacting a formyltyrosol lipophilic compound or composition thereof with a peroxide compound. Suitable lipophilic formyltyrosol esters can be represented by Formula 5:

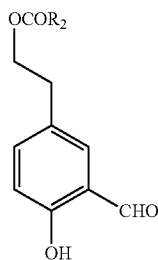

5 wherein $R_2$ is as described above.

The process for the manufacture of the lipophilic hydroxytyrosol esters and compositions thereof from lipophilic formyltyrosol esters are referred to herein as the peroxide oxidation process. The peroxide oxidation process proceeds desirably with an aqueous peroxide solution in an inert organic solvent in the presence of a base.

The organic solvent is chosen from cyclic or acyclic ether solvents such as diethyl ether, diisopropyl ether, tert-butyl methyl ether, or tetrahydrofuran; aromatic hydrocarbons such as benzene, toluene, or xylene; aliphatic, alicyclic, or alkaryl or alicyclic saturated or un-saturated hydrocarbons such as hexane, heptane, cyclohexane, or limonene; halogenated hydrocarbons such as dichloromethane, dichloroethane, dibromoethane, tetrachloroethylene, or chlorobenzene; polar aprotic solvents such as acetonitrile, dimethyl formamide, or dimethyl sulfoxide; alcohols such as methanol, ethanol, isopropyl alcohol or n-butanol; ketones such as acetone, diethyl ketone, or methyl isobutyl ketone, or mixtures thereof. In one embodiment of the invention isopropyl alcohol is used as the solvent.

The amount of solvent may be varied from about 1 part to about 20 parts of solvent per part of the lipophilic formyltyrosol ester or about 2 to 5 parts of solvent per part of lipophilic formyltyrosol ester substrate.

The peroxide can be any suitable peroxide or compound generating a peroxide. The peroxide may be organic or inorganic. Examples or organic peroxides include t-butyl hydroperoxide, cumene hydroperoxide, propionyl peroxide, acetyl peroxide, succinic acid peroxide, diacetyl peroxide, acetyl benzoyl peroxide, and mixtures thereof. Examples of inorganic peroxides include hydrogen peroxide, sodium peroxide, magnesium peroxide, calcium peroxide, zinc peroxide, mixed calcium/magnesium peroxides, sodium percarbonate and mixtures thereof.

The concentration of peroxide in the aqueous solution can be between about 1 and 80 wt. %, or about 10-50 wt. % based on the weight of the aqueous peroxide solution. In one embodiment of the invention the aqueous solution of peroxide is 30 to 40 wt. %, or about 33 wt. % to 37 wt. % peroxide. The amount of peroxide may be varied from about 0.9 to about 4 equivalents per equivalent of the lipophilic formyltyrosol ester substrate or about 1 to 2 equivalents. In one embodiment of the invention 1 to 2 equivalents of 30 to 40 wt. % hydrogen peroxide can be used.

The base used may be a mono or polyvalent metal hydroxide such as sodium hydroxide, potassium hydroxide, or calcium hydroxide; a mono or polyvalent metal carbonate such as potassium carbonate or calcium carbonate; a polyvalent oxide such as calcium oxide or magnesium oxide, a mono or polyvalent metal carboxylate such as sodium propionate or calcium acetate, a mono or polyvalent metal alkoxide such as sodium methoxide or magnesium methoxide, or a mono or polyvalent metal phosphate such as dibasic potassium phosphate or tribasic calcium phosphate. The amount base may be varied from about 0.9 to about 4 equivalents or 1 to 2 equivalents per equivalent of the formyltyrosol liphophilic compound. In one embodiment of the invention 1.2 equivalents of potassium hydroxide is used.

The peroxide oxidation process may be carried out at a temperature between about −100° C. and about 100° C. In one embodiment of the invention, the process is carried out at a temperature between about −100° C. and the boiling point of the solvent. Other suitable temperature ranges are from about 0° C. to about 60° C., and from about 0° C. to about 50° C., or from 15° C. to 45° C., or from 20° C. to 45° C. Optionally, the oxidation process can proceed without applied heat energy generated from a source external to the reaction medium. The process of the invention generates lipophilic hydroxytyrosol esters of Formula 6 from the peroxide oxidation of formyltyrosol lipophilic compounds of Formula 5 in yields of at least 70%, or at least 75%, or at least 80%, or at least 82%, or at least 85%, or at least 87%, or at least 89%, or at least 90%, or at least 91%, or at least 92%, or at least 93%, or at least 94%, or at least 95%, or at least 96%, and up to 99.5%, or up to 99.3%, or up to 99.0%, or up to 98.5%, or up to 98.0%, or up to 97.5%, or up to 97.0%, or up to 96.5%, or up to 96.0%, or up to 95.0%, or up to 94.0%, or up to 93.0%. The yield for the generation of any lipophilic hydroxytyrosol product of Formula 6 having a given $R_2$ group is calculated as follows:

$$\text{yield} = \frac{\text{moles of lipophilic hydroxytyrosol ester (Formula 6) made}}{\text{moles of liphopilic formyltyrosol esters (Formula 5) added}} \times 100$$

wherein $R_2$ is the same in Formula 5 and 6.

Examples of ranges of suitable yields include from 70% to 99.5%, or 75% to 99.5%, or 75% to 99.5%, or 80% to 99.5%, or 82% to 99.5%, or 85% to 99.5%, or 87% to 99.5%, or 89% to 99.5%, or 90% to 99.5%, or 91% to 99.5%, or 92% to 99.5%, or 93% to 99.5%, or 94% to 99.5%, or 95% to 99.5%, 70% to 99.3%, or 75% to 99.3%, or 75% to 99.3%, or 80% to 99.3%, or 82% to 99.3%, or 85% to 99.3%, or 87% to 99.3%, or 89% to 99.3%, or 90% to 99.3%, or 91% to 99.3%, or 92% to 99.3%, or 93% to 99.3%, or 94% to 99.3%, or 95% to 99.3%, or 70% to 99.0%, or 75% to 99.0%, or 75% to 99.0%, or 80% to 99.0%, or 82% to 99.0%, or 85% to 99.0%, or 87% to 99.0%, or 89% to 99.0%, or 90% to 99.0%, or 91% to 99.0%, or 92% to 99.0%, or 93% to 99.0%, or 94% to 99.0%, or 95% to 99.0%, or 70% to 98.5%, or 75% to 98.5%, or 75% to 98.5%, or 80% to 98.5%, or 82% to 98.5%, or 85% to 98.5%, or 87% to 98.5%, or 89% to 98.5%, or 90% to 98.5%, or 91% to 98.5%, or 92% to 98.5%, or 93% to 98.5%, or 94% to 98.5%, or 95% to 98.5%, or 70% to 98%, or 75% to 98%, or 75% to 985%, or 80% to 98%, or 82% to 98%, or 85% to 98%, or 87% to 98%, or 89% to 98%, or 90% to 98%, or 91% to 98%, or 92% to 98%, or 93% to 98%, or 94% to 98%, or 95% to 98%, or 70% to 97.5%, or 75% to 97.5%, or 75% to 97.5%, or 80% to 97.5%, or 82% to 97.5%, or 85% to 97.5%, or 87% to 97.5%, or 89% to 97.5%, or 90% to 97.5%, or 91% to 97.5%, or 92% to 97.5%, or 93% to 97.5%, or 94% to 97.5%, or 95% to 97.5%, or 70% to 97%, or 75% to 97%, or 75% to 97%, or 80% to 97%, or 82% to 97%, or 85% to 97%, or 87% to 97%, or 89% to 97%, or 90% to 97%, or 91% to 97%, or 92% to 97%, or 93% to 97%, or 94% to 97%, or 95% to 97%, or 70% to 96.5%, or 75% to 96.5%, or 75% to 96.5%, or 80% to 96.5%, or 82% to 96.5%, or 85% to 96.5%, or 87% to 96.5%, or 89% to 96.5%, or 90% to 96.5%, or 91% to 96.5%, or 92% to 96.5%, or 93% to 96.5%, or 94% to 96.5%, or 95% to 96.5%, or 70% to 96%, or 75% to 96%, or 75% to 96%, or 80% to 96%, or 82% to 96%, or 85% to 96%, or 87% to 96%, or 89% to 96%, or 90% to 96%, or 91% to 96%, or 92% to 96%, or 93% to 96%, or 94% to 96%, or 95% to 96%, or 70% to 95%, or 75% to 95%, or 75% to 95%, or 80% to 95%, or 82% to 95%, or 85% to 95%, or 87% to 95%, or 89% to 95%, or 90% to 95%, or 91% to 95%, or 92% to 95%, or 93% to 95%, or 94% to 95%, or 70% to 94%, or 75% to 94%, or 75% to 94%, or 80% to 94%, or 82% to 94%, or 85% to 94%, or 87% to 94%, or 89% to 94%, or 90% to 94%, or 91% to 94%, or 92% to 94%, or 93% to 94%, or 70% to 93%, or 75% to 93%, or 75% to 93%, or 80% to 93%, or 82% to 93%, or 85% to 93%, or 87% to 93%, or 89% to 93%, or 90% to 93%, or 91% to 93%, or 92% to 93%

The single step process of the invention to make the hydroxytyrosol ester of Formula 6 from lipophilic tyrosol ester Compound 5 can be performed to high selectivity with low formation of by-products, or in other words, to high selectivity towards the formation of the lipophilic hydroxytyrosol ester of Formula 6. Selectivity is calculated as follows:

$$\text{selectivity} = \frac{\text{moles of lipophilic hydroxytyrosol ester (Formula 6) made}}{\text{moles by-products made}} \times 100$$

wherein $R_2$ is the same in Formula 5 and 6.

The selectivity toward the production of lipophilic compounds of Formula 6 can be at least 70%, or at least 75%, or at least 80%, or at least 82%, or at least 85%, or at least 87%, or at least 89%, or at least 90%, or at least 91%, or at least 92%, or at least 93%, or at least 94%, or at least 95%, or at least 96%, and up to 99.5%, or up to 99.3%, or up to 99.0%, or up to 98.5%, or up to 98.0%, or up to 97.5%, or up to 97.0%, or up to 96.5%, or up to 96.0%, or up to 95.0%, or up to 94.0%, or up to 93.0%.

Examples of ranges of suitable selectivity values include from 70% to 99.5%, or 75% to 99.5%, or 75% to 99.5%, or 80% to 99.5%, or 82% to 99.5%, or 85% to 99.5%, or 87% to 99.5%, or 89% to 99.5%, or 90% to 99.5%, or 91% to 99.5%, or 92% to 99.5%, or 93% to 99.5%, or 94% to 99.5%, or 95% to 99.5%, 70% to 99.3%, or 75% to 99.3%, or 75% to 99.3%, or 80% to 99.3%, or 82% to 99.3%, or 85% to 99.3%, or 87% to 99.3%, or 89% to 99.3%, or 90% to 99.3%, or 91% to 99.3%, or 92% to 99.3%, or 93% to 99.3%, or 94% to 99.3%, or 95% to 99.3%, or 70% to 99.0%, or 75% to 99.0%, or 75% to 99.0%, or 80% to 99.0%, or 82% to 99.0%, or 85% to 99.0%, or 87% to 99.0%, or 89% to 99.0%, or 90% to 99.0%, or 91% to 99.0%, or 92% to 99.0%, or 93% to 99.0%, or 94% to 99.0%, or 95% to 99.0%, or 70% to 98.5%, or 75% to 98.5%, or 75% to 98.5%, or 80% to 98.5%, or 82% to 98.5%, or 85% to 98.5%, or 87% to 98.5%, or 89% to 98.5%, or 90% to 98.5%, or 91% to 98.5%, or 92% to 98.5%, or 93% to 98.5%, or 94% to 98.5%, or 95% to 98.5%, or 70% to 98%, or 75% to 98%, or 75% to 985%, or 80% to 98%, or 82% to 98%, or 85% to 98%, or 87% to 98%, or 89% to 98%, or 90% to 98%, or 91% to 98%, or 92% to 98%, or 93% to 98%, or 94% to 98%, or 95% to 98%, or 70% to 97.5%, or 75% to 97.5%, or 75% to 97.5%, or 80% to 97.5%, or 82% to 97.5%, or 85% to 97.5%, or 87% to 97.5%, or 89% to 97.5%, or 90% to 97.5%, or 91% to 97.5%, or 92% to 97.5%, or 93% to 97.5%, or 94% to 97.5%, or 95% to 97.5%, or 70% to 97%, or 75% to 97%, or 75% to 97%, or 80% to 97%, or 82% to 97%, or 85% to 97%, or 87% to 97%, or 89% to 97%, or 90% to 97%, or 91% to 97%, or 92% to 97%, or 93% to 97%, or 94% to 97%, or 95% to 97%, or 70% to 96.5%, or 75% to 96.5%, or 75% to 96.5%, or 80% to 96.5%, or 82% to 96.5%, or 85% to 96.5%, or 87% to 96.5%, or 89% to 96.5%, or 90% to 96.5%, or 91% to 96.5%, or 92% to 96.5%, or 93% to 96.5%, or 94% to 96.5%, or 95% to 96.5%, or 70% to 96%, or 75% to 96%, or 75% to 96%, or 80% to 96%, or 82% to 96%, or 85% to 96%, or 87% to 96%, or 89% to 96%, or 90% to 96%, or 91% to 96%, or 92% to 96%, or 93% to 96%, or 94% to 96%, or 95% to 96%, or 70% to 95%, or 75% to 95%, or 75% to 95%, or 80% to 95%, or 82% to 95%, or 85% to 95%, or 87% to 95%, or 89% to 95%, or 90% to 95%, or 91% to 95%, or 92% to 95%, or 93% to 95%, or 94% to 95%, or 70% to 94%, or 75% to 94%, or 75% to 94%, or 80% to 94%, or 82% to 94%, or 85% to 94%, or 87% to 94%, or 89% to 94%, or 90% to 94%, or 91% to 94%, or 92% to 94%, or 93% to 94%, or 70% to 93%, or 75% to 93%, or 75% to 93%, or 80% to 93%, or 82% to 93%, or 85% to 93%, or 87% to 93%, or 89% to 93%, or 90% to 93%, or 91% to 93%, or 92% to 93%

The production of high yields of lipophilic hydroxytyrosol ester of Formula 6 allows one the flexibility to isolate this product, such as through precipitation, without the necessity of employing costly separation processes prior to isolating this product. After the lipophilic hydroxytyrosol ester is isolated, it can be refined to further purify the composition.

The process of the invention also has the advantage in that it can be readily scaled up to make large quantities of the lipophilic hydroxytyrosol ester and the lipophilic hydroxytyrosol carbonate ester because of the ease by which the lipophilic hydroxytyrosol ester can be isolated, and the solvent used is safer, cheaper, and readily adaptable to scale up compared to dichloromethane, and the peroxide reagent is readily available, inexpensive, safer and less expensive than 3-chloroperbenzoic acid.

The lipophilic hydroxytyrosol carbonate esters of Formula 2 compounds and compositions have an advantage in that they can be more easily hydrolyzed, such as through enzymatic hydrolysis with facial moisture or cellular water, compared to equivalent hydroxytyrosol esters having only ester blocking groups and devoid of carbonate groups. Thus, the lipophilic hydroxytyrosol carbonate esters of Formula 2 are not only stable in fatty carriers due to the presence of the R₂ lipophilic group, but upon contact with keratinous tissue such as skin, can then by hydrolyzed to the active form of lipophilic hydroxytyrosol esters of Formula 6 or to hydroxytyrosol itself.

Any suitable process can be used to obtain a lipophilic formyltyrosol ester. For example, a lipophilic ester of 4-(2-hydroxyethyl)phenol represented by Formula 4 can be reacted with formaldehyde, or a substance that can generate formaldehyde, to produce the lipophilic formyltyrosol ester. The reaction desirably proceeds in a solvent and in the presence of a polyvalent anhydrous metal halide and an organic base. The lipophilic ester of 4-(2-hydroxyethyl)phenol is represented by the following Formula 4:

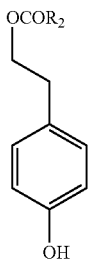

4 wherein $R_2$ has the same meaning as $R_2$ above.

The organic solvent is chosen from cyclic or acyclic ether solvents, such as diethyl ether, diisopropyl ether, tert-butyl methyl ether, or tetrahydrofuran; aromatic hydrocarbons, such as, benzene, toluene, or xylene; aliphatic, alicyclic, or alkaryl or alicyclic saturated or unsaturated hydrocarbons, such as, hexane, heptane, or cyclohexane, halogenated hydrocarbons, such as, dichloromethane, dichloroethane, dibromoethane, tetrachloroethylene, or chlorobenzene; polar aprotic solvents, such as, acetonitrile, dimethyl formamide, or dimethyl sulfoxide. In one embodiment of the invention tetrahydrofuran is used as the solvent. The amount of solvent may be varied from about 1 part to about 20 parts of solvent per part of the lipophilic ester of 4-(2-hydroxyethyl)phenol, or about 2 to 5 parts of solvent per part of the lipophilic ester of 4-(2-hydroxyethyl)phenol.

The source of the formaldehyde may be gaseous anhydrous formaldehyde, or a substance that can generate the same, such as 1,3,5-trioxane or paraformaldehyde, with paraformaldehyde preferred. The amount of formaldehyde or formaldehyde-generating material may be varied between mole and 10 moles, or 6-7 moles, per mole of the lipophilic ester of 4-(2-hydroxyethyl)phenol.

The anhydrous polyvalent metal halide can be any that forms strong bonds with phenoxide ions and with formaldehyde, such as aluminum (III) chloride, copper (II) bromide, iron (III) chloride, tin (IV) chloride, tin (II) chloride, or magnesium (II) chloride, with magnesium (II) chloride preferred. Depending on the anhydrous polyvalent metal halide used, the amount needed can be between 0.05 and 5 moles of metal halide per mole of lipophilic ester of 4-(2-hydroxyethyl)phenol. With the preferred anhydrous polyvalent metal halide magnesium (II) chloride, the preferred amount is 1.5-2 moles of magnesium (II) chloride per mole of lipophilic ester of 4-(2-hydroxyethyl)phenol.

The organic base can be an aromatic one, such as pyridine, 2-6-dimethylpyridine, or quinoline, or it can be a cyclic or acyclic tertiary amine base such as 1,8-diazabicyclo[5.4.0] undec-7-ene, trioctylamine, tributylamine, diisopropylethylamine, or triethylamine, with triethylamine preferred. Depending on the anhydrous polyvalent metal halide used, the amount of organic base needed can be between 0.05 and 5 moles, or 3 to 4 moles, of base per mole of lipophilic ester of 4-(2-hydroxyethyl)phenol. For example, one may use an anhydrous polyvalent metal halide such as magnesium (II) chloride with 3 to 4 moles of base per mole of the lipophilic ester of 4-(2-hydroxyethyl)phenol.

The process for reacting the lipophilic ester of 4-(2-hydroxyethyl)phenol to make a formyltyrosol lipophilic compound may be carried out at a temperature between about 0° C. and the boiling point of the solvent, or about 0-70° C. or about 40-60° C.

The lipophilic formyltyrosol ester may be isolated using methods known to those of skill in the art, e.g., by extraction, filtration, or crystallization.

Any suitable process can be employed to make the lipophilic ester 4 of 4-(2-hydroxyethyl)phenol, which is also known as tyrosol. For example, the liphophilic group that one selects can be attached by reacting a carboxylic acid or its short chain ester represented by Formula 8 having the desired number of carbon atoms with 4-(2-hydroxyethyl)phenol, as represented by Formula 3, in the presence of lipase, esterase, or protease:

$R_2CO_2X$

8

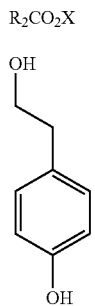

3 wherein $R_2$ has the same meaning as noted above, and X is selected from hydrogen or $C_1$-$C_5$ straight or branched chain primary or secondary alkane or alkene.

The process for making the lipophilic ester of 4-(2-hydroxyethyl)phenol is carried out without solvent or in an inert solvent chosen from cyclic or acyclic ether solvents. Examples of such solvents include diethyl ether, diisopropyl ether, tert-butyl methyl ether, or tetrahydrofuran; aromatic hydrocarbons such as benzene, toluene, or xylene; aliphatic, alicyclic, or alkaryl or alicyclic saturated or unsaturated hydrocarbons such as hexane, heptane, or cyclohexane; halogenated hydrocarbons such as dichloromethane, dichloroethane, dibromoethane, tetrachloroethylene, or chlorobenzene; ketones such as acetone. diethyl ketone. or methyl isobutyl ketone; tertiary alcohols such as tert-butanol or tert-pentanol; polar aprotic solvents such as acetonitrile, dimethyl formamide, or dimethyl sulfoxide, or mixtures thereof. The preferred solvents are no solvent, toluene, heptanes, acetone, and acetonitrile.

The process may be carried out at a temperature between about −100° C. and the boiling point of the solvent, or about 0-70° C., or 55-65° C.

The amount of short chain ester or acid of Formula 8 may be between 0.85 and 1.5 equivalents based on tyrosol, or between 1 and 1.25 equivalents, or between 1 and 1.1 equivalents.

The enzyme used in the process may be chosen from a variety of hydrolytic enzymes, for example a protease, a lipase, or an esterase. Preferred enzymes include lipases. These lipases may be in the form of whole cells, isolated native enzymes, or immobilized on supports.

Examples of suitable lipases include, but are not limited to, Lipase PS (from *Pseudomonas* sp), Lipase PS-C (from *Pseudomonas* sp immobilized on ceramic), Lipase PS-D (from *Pseudomonas* sp immobilized on diatomaceous earth), Lipoprime 50T, Lipozyme TL IM, or Novozyme 435 (*Candida antarctica* lipase B immobilized on acrylic resin). Removal of the water or alcohol byproducts, if desired, can be done chemically by a water or alcohol absorbent (e.g., molecular sieves) or by physical removal of the water or alcohol. This by-product removal is preferably done by evaporation, either by purging the reaction mixture with an inert gas such as nitrogen, argon, or helium, or by performing the reaction at reduced pressures, or both, as these conditions can afford >95% conversion of 4-(2-hydroxyethyl)phenol (3) (tyrosol) to its lipophilic ester (4). The preferred pressure for the reaction is between 1 torr and ambient pressure, more preferable between 20 torr and ambient pressure. Any organic solvent that is included in this process may or may not be removed along with the water or alcohol.

The lipophilic ester of 4-(2-hydroxyethyl)phenol may be isolated using methods known to those of skill in the art, e.g., by extraction, filtration, or crystallization.

The invention has the advantage of providing an improved process for the manufacture of compounds represented by Formula 6 by reacting a lipophilic formyltyrosoi ester with a peroxide, which is a practical synthesis utilizing readily available starting materials (e.g. peroxides). This synthesis is suitable for scale-up to kilogram quantities. This synthesis is also easily adapted to simple changes in the $R_2$ carboxylate functionality and in the selection of types of carbonate esters.

The lipophilic hydroxytyrosol carbonate ester compounds of Formula 2 and compositions according to the present invention can be used in personal care compositions, such as cosmetic compositions, skin care compositions, hair products, and the like. The lipophilic hydroxytyrosol carbonate ester compounds and compositions can be useful, for example, for reducing at least one of skin roughness, fine lines, or wrinkles, or improving photo-damaged skin, or regenerating skin, or reducing skin hyper-pigmentation, or reducing irritation and inflammatory reactions in skin.

Personal care compositions are for topical application to a keratinous surface, and contain the liphophilic hydroxytyrosol carbonate ester compounds and compositions, and for brevity, are referred to throughout as personal care compositions. The personal care compositions can be topically applied to humans and animals, but desirably include personal care applications to humans. The personal care products can be left on or rinsed off. Personal care compositions include cosmetic compositions (including color cosmetics), baby care compositions, bath and shower compositions, skin care compositions, sun care compositions, hair care compositions, hygiene compositions, depilatory compositions, and fragrance compositions. In one embodiment, personal care compositions do not include oral care compositions or compositions which are topically applied to the mouth cavity (e.g. gums and teeth). In another embodiment, personal care compositions do not include liquid fragrance compositions having a viscosity of less than 1 cps. In another embodiment, the personal care compositions do not include solid hygiene products other than deodorants.

The personal care compositions can contain at least 0.001 wt. % by weight of the lipophilic hydroxytyrosol carbonate ester compounds, based on the weight of the personal care composition. For example, there is a provided a personal care compositions comprising at least 0.001 wt. %, or at least 0.005 wt. %, or at least 0.01 wt. %, or at least 0.05 wt. %, or at least 0.1 wt. %, or at least 0.5 wt. %, or at least 1.0 wt. %, or at least 1.5 wt. %, or at least 2 wt. %, or at least 2.5 wt. %, or at least 3 wt. %, or at least 3.5 wt. %, or at least 4 wt. %, or at least 4.5 wt. %, or at least 5 wt. %, or at least 5.5 wt. %, or at least 6 wt. %, or at least 6.5 wt. %, or at least 7 wt. %, or at least 8 wt. %, or at least 9 wt. %, or at least 10 wt. % of the lipophilic hydroxytyrosol carbonate ester compounds, based on the weight of the personal care composition. The personal care compositions can contain up to 20 wt. %, or up to 19 wt. %, or up to 18 wt. %, or up to 17 wt. %, or up to 16 wt. %, or up to 15 wt. %, or up to 14 wt. %, or up to 13 wt. %, or up to 12 wt. %, or up to 11 wt. %, or up to 10 wt. %, or up to 9 wt. %, or up to 8 wt. %, or up to 7 wt. %, or up to 6 wt. %, or up to 5 wt. %, or up to 4 wt. %, or up to 3 wt. %, or up to 2.5 wt. %, or up to 2 wt. %, or up to 1.5 wt. %, or up to 1 wt. %, or up to 0.5 wt. % of the lipophilic hydroxytyrosol carbonate ester compounds, based on the weight of the personal care composition.

The lower concentrations may be employed for less pronounced conditions, and higher concentrations may be employed with more acute conditions. Suggested ranges also depend upon any adjunct ingredients employed in the compositions. Examples of suitable ranges include 0.001 wt % to 20 wt. %, or 0.001 wt. % to 15 wt. %, or 0.001 wt. % to 10 wt. %, or 0.001 wt. % to 7 wt. %, or 0.001 wt. % to 5 wt. %, or 0.001 wt. % to 4 wt. %, or 0.001 wt. % to 3 wt. %, or 0.001 wt. % to 2.5 wt. %, or 0.001 wt. % to 2 wt. %, or 0.001 wt. % to 1.5 wt. %, or 0.001 wt. % to 1 wt. %, or 0.001 wt. % to 0.5 wt. %, or 0.005 wt. % to 20 wt. %, or 0.005 wt. % to 15 wt. %, or 0.005 wt. % to 10 wt. %, or 0.005 wt. % to 7 wt. %, or 0.005 wt. % to 5 wt. %, or 0.005 wt. % to 4 wt. %, or 0.005 wt. % to 3 wt. %, or 0.005 wt. % to 2.5 wt. %, or 0.005 wt. % to 2 wt. %, or 0.005 wt. % to 1.5 wt. %, or 0.005 wt. % to 1 wt. %, or 0.005 wt. % to 0.5 wt. %, or 0.01 wt. % to 20 wt. %, or 0.01 wt. % to 15 wt. %, or 0.01 wt. % to 10 wt. %, or 0.01 wt. % to 7 wt. %, or 0.01 wt. % to 5 wt. %, or 0.01 wt. % to 4 wt. %, or 0.01 wt. % to 3 wt. %, or 0.01 wt. % to 2.5 wt. %, or 0.01 wt. % to 2 wt. %, or 0.01 wt. % to 1.5 wt. %, or 0.01 wt. % to 1 wt. %, or 0.01 wt. % to 0.5 wt. %, or 0.05 wt. % to 20 wt. %, or 0.05 wt. % to 15 wt. %, or 0.05 wt. % to 10 wt. %, or 0.05 wt. % to 7 wt. %, or 0.05 wt. % to 5 wt. %, or 0.05 wt. % to 4 wt. %, or 0.05 wt. % to 3 wt. %, or 0.05 wt. % to 2.5 wt. %, or 0.05 wt. % to 2 wt. %, or 0.05 wt. % to 1.5 wt. %, or 0.05 wt. % to 1 wt. %, or 0.05 wt. % to 0.5 wt. %, or 0.1 wt. % to 20 wt. %, or 0.1 wt. % to 15 wt. %, or 0.1 wt. % to 10 wt. %, or 0.1 wt. % to 7 wt. %, or 0.1 wt. % to 5 wt. %, or 0.1 wt. % to 4 wt. %, or 0.1 wt. % to 3 wt. %, or 0.1 wt. % to 2.5 wt. %, or 0.1 wt. % to 2 wt. %, or 0.1 wt. % to 1.5 wt. %, or 0.1 wt. % to 1 wt. %, or 0.1 wt. % to 0.5 wt. %, or 0.5 wt. % to 20 wt. %, or 0.5 wt. % to 15 wt. %, or 0.5 wt. % to 10 wt. %, or 0.5 wt. % to 7 wt. %, or 0.5 wt. % to 5 wt. %, or 0.5 wt. % to 4 wt. %, or 0.5 wt. % to 3 wt. %, or 0.5 wt. % to 2.5 wt. %, or 0.5 wt. % to 2 wt. %, or 0.5 wt. % to 1.5 wt. %, or 0.5 wt. % to 1 wt. %, or 0.5 wt. % to 0.5 wt. %, or 1 wt. % to 20 wt. %, or 1 wt. % to 15 wt. %, or 1 wt. % to 10 wt. %, or 1 wt. % to 7 wt. %, or 1 wt. % to 5 wt. %, or 1 wt. % to 4 wt. %, or 1 wt. % to 3 wt. %, or 1 wt. % to 2.5 wt. %, or 1 wt. % to 2 wt. %, or 1 wt. % to 1.5 wt. %, or 1.5 wt. % to 20 wt. %, or 1.5 wt. % to 15 wt. %, or 1.5 wt. % to 10 wt. %, or 1.5 wt. % to 7 wt. %, or 1.5 wt. % to 5 wt. %, or 1.5 wt. % to 4 wt. %, or 1.5 wt. % to 3 wt. %, or 1.5 wt. % to 2.5 wt. %, or 1.5 wt. % to 2 wt. %, or 2 wt. % to 20 wt. %, or 2 wt. % to 15 wt. %, or 2 wt. % to 10 wt. %, or 2 wt. % to 7 wt. %, or 2 wt. % to 5 wt. %, or 2 wt. % to 4 wt. %, or 2 wt. % to 3 wt. %, or 3 wt. % to 20 wt. %, or 3 wt. % to 15 wt. %, or 3 wt. % to 10 wt. %, or 3 wt. % to 7 wt. %, or 3 wt. % to 5 wt. %, or 3 wt. % to 4 wt. %, or 4 wt. % to 20 wt. %, or 4 wt. % to 15 wt. %, or 4 wt. % to 10 wt. %, or 4 wt. % to 7 wt. %, or 4 wt. % to 5 wt. % or 5 wt. % to 20 wt. %, or 5 wt. % to 15 wt. %, or 5 wt. % to 10 wt. %, or 5 wt. % to 7 wt. %, or 7 wt. % to 20 wt. %, or 7 wt. % to 15 wt. %, or 7 wt. % to 10 wt. %, or 10 wt. % to 20 wt. %, or 10 wt. % to 15 wt. %.

Examples of cosmetic compositions include nail care compositions such as nail (finger and toe) polish and nail polish removers, and makeup products that contain a color deposited onto a keratinous substrate such as skin, lips, and lashes. Makeup products include primers, lipstick, lip gloss, lip plumper, lip liners, lip balms, eyeliners, eyeshadows, masara, concealers, rouges, foundations, face powders, highlighters, contour powders or creams, bronzers, eyebrow definers, and setting sprays for makeup. The cosmetic compositions can be in many different forms, including liquid or cream emulsions; powders that are pressed, cast, or loose; dispersions, and anhydrous creams or sticks; or solids such as pencils and the aforementioned powders and sticks.

Examples of shower and bath compositions containing the liphophilic hydroxytyrosol carbonate ester compounds include but are not limited to body washes (including moisturizing body wash), shower gels, skin cleansers, cleansing milks, in shower body moisturizer, and pet shampoo.

Examples of hair care compositions include shampoos, hair conditioners, colorants. dyes, bleaches, straighteners, and permanent wave products.

Examples of infant care compositions include infant shampoo, infant body wash, and infant bubble bath.

Examples of skin care compositions include shaving compositions, cleansing compositions, emollients, moisturizing compositions including anti-aging compositions; exfoliant compositions, face masks, and skin toners, and compositions containing pharmaceutically active ingredients for reduction of skin irritations, rashes, inflammations, and excema.

Examples of sun care compositions include compositions containing UV blocking agents (UVA and/or UVB), such as sun tan compositions, sunscreen compositions having an SPF rating of 20 or more, or 30 or more, or 40 or more, or 50 or more; and lip balms and lip care for protection against wind and sun . Sun care compositions may also include sunless tanning treatments. These may be in the form of lotions, oils, creams, gels, and sprays.

The personal care compositions comprising liphophilic hydroxytyrosol carbonate ester compounds can include additional ingredients depending upon the desired application. The personal care compositions may contain, in addition to the liphophilic hydroxytyrosol carbonate ester compounds, carriers, cleansing agents, emollients, moisturizers or hydrating agents, active anti-aging or anti-wrinkle agents, pigments, colorants, fragrances, biocides, preservatives, antioxidants, antiperspirant agents, exfoliants, hormones, enzymes, medicinal compounds, vitamins, ultraviolet light absorbers, skin bleaching agents, anti-acne agents, botanical extracts, silicone ohs, organic oils, waxes, adhesion promoters, plasticizers, film formers, including hair fixatives, thickening agents, fillers and binders, alcohol and other organic solvents, and propellants.

Carriers or Vehicles

The personal care compositions may comprise a liphophilic hydroxytyrosol carbonate ester compound and a carrier. Carriers are inert in the sense of not bringing about a deactivation or oxidation of the carbonate ester. The carrier can be a single compound, a polymer, or a composition of several ingredients and compounds. Desirably, carriers are also dermatologically acceptable.

The liphophilic hydroxytyrosol carbonate ester compounds can be applied in admixture with a dermatologically acceptable carrier or vehicle (e.g., as a lotion, cream, ointment, soap, stick, or the like) so as to facilitate topical application and, in some cases, provide additional beneficial effects as might be brought about, e.g., by moisturizing of the affected skin areas. Many preparations are known in the art, and include lotions containing oils and/or alcohols and emollients.

Suitable carriers include olive oil, hydrocarbon oils and waxes, silicone oils, other vegetable, animal or marine fats or oils, glyceride derivatives, fatty acids or fatty acid esters or alcohols or alcohol ethers, fatty acid salts, lecithin, lanolin and derivatives, polyhydric alcohols or esters (e.g. glycols and their esters), wax esters, sterols, alkyl benzoates, phospholipids and the like, and combinations thereof. Carriers can also be emulsions containing emulsifiers (nonionic, cationic or anionic). The emulsions can be oil in water or water in oil. These same general ingredients can be formulated into a cream rather than a lotion, or as solutions including aqueous or hydro-alcoholic, anhydrous bases such as lipsticks and powders, milks, aerosols, gels, ointments, pastes, or into solid sticks by utilization of different proportions of the ingredients and/or by inclusion of thickening agents such as gums or other forms of hydrophilic colloids.

The carrier may also encapsulate the lipophilic hydroxytyrosol carbonate ester compound or any other ingredient for targeted or timed delivery. Non-limiting examples of encapsulation techniques include the use of liposomes, vesicles, and/or nanoparticles (e.g., biodegradable and non-biodegradable colloidal particles comprising polymeric materials in which the ingredient is trapped, encapsulated, and/or absorbed. Examples include nanospheres and nanocapsules that can be used as delivery vehicles to deliver ingredients to skin.

The personal care composition may contain, in addition to the liphophilic hydroxytyrosol carbonate ester compounds, from 0.001 wt. % to 20 wt. %, or at least 0.01 wt. %, or at least 0.1 wt. %, or at least 0.5 wt. %, or at least 1 wt. %, and up to 20 wt. %, or up to 15 wt. %, or up to 10 wt. %, or up to 8 wt. %, or up to 5 wt. % of any one of the above described carriers, based on the weight of the personal care composition. Examples of suitable ranges include a personal care composition comprising, in addition to the liphophilic hydroxytyrosol carbonate ester compounds, a carrier present in an amount of from 0.001 wt. % to 20 wt. %, or 0.001 wt. % to 15 wt. %, or 0.001 wt. % to 10 wt. %, or 0.001 wt. % to 8 wt. %, or 0.001 wt. % to 5 wt. %, or 0.01 wt. % to 20 wt. %, or 0.01 wt. % to 15 wt. %, or 0.01 wt. % to 10 wt. %, or 0.01 wt. % to 8 wt. %, or 0.01 wt. % to 5 wt. %, or 0.1 wt. % to 20 wt. %, or 0.1 wt. % to 15 wt. %, or 0.1 wt. % to 10 wt. %, or 0.1 wt. % to 8 wt. %, or 0.1 wt. % to 5 wt. %, or 0.5 wt. % to 20 wt. %, or 0.5 wt. % to 15 wt. %, or 0.5 wt. % to 10 wt. %, or 0.5 wt. % to 8 wt. %, or 0.5 wt. % to 5 wt. %, or 1 wt. % to 20 wt. %, or 1 wt. % to 15 wt. %, or 1 wt. % to 10 wt. %, or 1 wt. % to 8 wt. %, or 1 wt. % to 5 wt. %, in each case based on the weight of the personal care composition.

The personal care composition can comprise a fatty phase. The fatty phase can comprise one or more of the carriers. The personal care composition can comprise a fatty phase in an amount of 5 to 99 wt. %, or 40 to 99 wt. %, or 50 to 99 wt. %, or 60 to 99 wt. %, or 70 to 99 wt. %, based on the weight of the composition.

Cleansing Agents

The personal care compositions of the invention may include liphophilic hydroxytyrosol carbonate ester compounds and a cleansing agent. A cleansing agent assists in the removal of living or nonliving matter from the surface of skin. Suitable cleansing agents include lauryl glucoside, decyl glucoside, cocamidopropyl Betaine, coco-Glucoside, polyglucose, sodium coco sulfate, alcohol, and lemon oil.

The personal care composition may contain, in addition to the liphophilic hydroxytyrosol carbonate ester compounds, from 0.001 wt. % to 20 wt. %, or at least 0.01 wt. %, or at least 0.1 wt. %, or at least 0.5 wt. %, or at least 1 wt. %, and up to 20 wt. %, or up to 15 wt. %, or up to 10 wt. %, or up to 8 wt. %, or up to 5 wt. % of a cleansing agent, based on the weight of the personal care composition. Examples of suitable ranges include a personal care composition comprising, in addition to a liphophilic hydroxytyrosol carbonate ester compound, a cleansing agent present in an amount of from 0.001 wt. % to 20 wt. %, or 0.001 wt. % to 15 wt. %, or 0.001 wt. % to 10 wt. %, or 0.001 wt. % to 8 wt. %, or 0.001 wt. % to 5 wt. %, or 0.01 wt. % to 20 wt. %, or 0.01 wt. % to 15 wt. %, or 0.01 wt. % to 10 wt. %, or 0.01 wt. % to 8 wt. %, or 0.01 wt. % to 5 wt. %, or 0.1 wt. % to 20 wt. %, or 0.1 wt. % to 15 wt. %, or 0.1 wt. % to 10 wt. %, or 0.1 wt. % to 8 wt. %, or 0.1 wt. % to 5 wt. %, or 0.5 wt. % to 20 wt. %, or 0.5 wt. % to 15 wt. %, or 0.5 wt. % to 10 wt. %, or 0.5 wt. % to 8 wt. %, or 0.5 wt. % to 5 wt. %, or 1 wt. % to 20 wt. %, or 1 wt. % to 15 wt. %, or 1 wt. % to 10 wt. %, or 1 wt. % to 8 wt. %, or 1 wt. % to 5 wt. %, in each case based on the weight of the personal care composition.

Emollients

The personal care compositions of the invention may include liphophilic hydroxytyrosol carbonate ester compounds and an emolient. Suitable emolients include glyceryl stearate, isopropyl palmitate, ethylhexyi paimitate, cetyl esters, isopropyl myristate, isopropyl isostearate, myristyl myristate, cetyl palmitate, glyceryl oleate, hexyl iaurate, isononyi isononanoate, dicapryl malate, diisostearyl malate, cetyl acetate, ethylhexyl stearate, oleyl oleate, cetyl ricinoleate, and cetyl ethyihexanoate.

The personal care composition may contain, in addition to the liphophilic hydroxytyrosol carbonate ester compounds, from 0.001 wt. % to 20 wt. %, or at least 0.01 wt. %, or at least 0.1 wt. %, or at least 0.5 wt. %, or at least 1 wt. %, and up to 20 wt. %, or up to 15 wt. %, or up to 10 wt. %, or up to 8 wt. %, or up to 5 wt. % of an emolient, based on the weight of the personal care composition. Examples of suitable ranges include a personal care composition comprising, in addition to a liphophilic hydroxytyrosol carbonate ester compound, an emolient present in an amount of from 0.001 wt. % to 20 wt. %, or 0.001 wt. % to 15 wt. %, or 0.001 wt. % to 10 wt. %, or 0.001 wt. % to 8 wt. %, or 0.001 wt. % to 5 wt. %, or 0.01 wt. % to 20 wt. %, or 0.01 wt. % to 15 wt. %, or 0.01 wt. % to 10 wt. %, or 0.01 wt. % to 8 wt. %, or 0.01 wt. % to 5 wt. %, or 0.1 wt. % to 20 wt. %, or 0.1 wt. % to 15 wt. %, or 0.1 wt. % to 10 wt. %, or 0.1 wt. % to 8 wt. %, or 0.1 wt. % to 5 wt. %, or 0.5 wt. % to 20 wt. %, or 0.5 wt. % to 15 wt. %, or 0.5 wt. % to 10 wt. %, or 0.5 wt. % to 8 wt. %, or 0.5 wt. % to 5 wt. %, or 1 wt. % to 20 wt. %, or 1 wt. % to 15 wt. %, or 1 wt. % to 10 wt. %, or 1 wt. % to 8 wt. %, or 1 wt. % to 5 wt. %, in each case based on the weight of the personal care composition.

Moisturization, Hydration and Skin Conditioning Agents

The personal care compositions of the invention may include liphophilic hydroxytyrosol carbonate ester compounds and a moisturizing agent (which includes a hydration and skin conditioner). Suitable moisturizing agents include glycerin, butyrospermum parkii (rhea butter), aloe extracts, allantoin, bisaboloi, ceramides, dimethicone, hyaluronic acid, dipotassium glycyrrhizate, amino acids, chondroitin sulfate, diglycerin, erythritol, fructose, glucose, glycerol polymers, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrollidone carboxylic acid, potassium PCA, propylene glycol, sodium glucuronate, sodium PCA, sorbitol, sucrose, trehalose, urea, xylitol, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG40 sorbitan peroleate, PEG-5 soy sterol, PEG-10 soy sterol, PEG-2 stearate, PEG-8 stearate, PEG-20 stearate, PEG-32 stearate, PEG40 stearate, PEG-50 stearate, PEG-100 stearate, PEG-150 stearate, polysorbate 20, poiysorbate 40, polysorbate 60, polysorbate 80, polysorbate 85, potassium myristate, potassium palmitate, potassium sorbate, potassium stearate, propylene glycol, propylene glycol dicaprylateidicaprate, propylene glycol dioctanoate, propylene glycol dipelargonate, propylene glycol laurate, propylene glycol stearate, propylene glycol stearate SE, PVP, pyridoxine dipalmitate, quaternium-15, quaternium-18 hectorite, quaternium-22, retinol, retinyl palmitate, rice (*oryza sativa*) bran oil, RNA, rosemary (*rosmarinus officinalis*) oil, rose oil, safflower (*carthamus tinctorius*) oil, sage (*salvia officinalis*) oil, salicylic acid, sandalwood (*santalum album*) oil, serine, serum protein, sesame (*sesamum indicum*) oil, silk powder, sodium chondroitin sulfate, sodium hyaluronate, sodium lactate, sodium palmitate, sodium PCA, sodium polyglutamate, sodium stearate, soluble collagen, sorbic acid, sorbitan laurate, sorbitan oleate, sorbitan palmitate, sorbitan sesquioleate, sorbitan stearate, sorbitol, soybean (*glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*helianthus annuus*) seed oil, sweet almond (*prunus amygdalus dulcis*) oil, synthetic beeswax, tocopheryl linoleate, tribehenin, tridecyi neopentanoate, tridecyi stearate, triethanolamine, tristearin, urea, vegetable oil, water, waxes, wheat (*triticum vulgare*) germ oil, and ylang ylang (*cananga odorata*) oil.

The personal care composition may contain, in addition to the liphophilic hydroxytyrosol carbonate ester compounds, from 0.001 wt. % to 20 wt. %, or at least 0.01 wt. %, or at least 0.1 wt. %, or at least 0.5 wt. %, or at least 1 wt. %, and up to 20 wt. %, or up to 15 wt. %, or up to 10 wt. %, or up to 8 wt. %, or up to 5 wt. % of a moisturizing agent, based on the weight of the personal care composition. Examples of suitable ranges include a personal care composition comprising, in addition to a liphophilic hydroxytyrosol carbonate ester compound, a moisturizing agent present in an amount of from 0.001 wt. % to 20 wt. %, or 0.001 wt. % to 15 wt. %, or 0.001 wt. % to 10 wt. %, or 0.001 wt. % to 8 wt. %, or 0.001 wt. % to 5 wt. %, or 0.01 wt. % to 20 wt. %, or 0.01 wt. % to 15 wt. %, or 0.01 wt. % to 10 wt. %, or 0.01 wt. % to 8 wt. %, or 0.01 wt. % to 5 wt. %, or 0.1 wt. % to 20 wt. %, or 0.1 wt. % to 15 wt. %, or 0.1 wt. % to 10 wt. %, or 0.1 wt. % to 8 wt. %, or 0.1 wt. % to 5 wt. %, or 0.5 wt. % to 20 wt. %, or 0.5 wt. % to 15 wt. %, or 0.5 wt. % to 10 wt. %, or 0.5 wt. % to 8 wt. %, or 0.5 wt. % to 5 wt. %, or 1 wt. % to 20 wt. %, or 1 wt. % to 15 wt.

%, or 1 wt. % to 10 wt. %, or 1 wt. % to 8 wt. %, or 1 wt. % to 5 wt. %, in each case based on the weight of the personal care composition.

Active Anti-Aging or Anti-Wrinkle Agents

The personal care compositions of the invention may include liphophilic hydroxytyrosol carbonate ester compounds and an anti-aging agents. Examples of anti-aging agents include retinal, retinyl esters, tetronic acid, tetronic acid derivatives, hydroquinone, kojic acid, gallic acid, arbutin, α-hydroxy acids, and fatty acid esters of ascorbic acid.

The personal care composition may contain, in addition to the liphophilic hydroxytyrosol carbonate ester compounds, from 0.001 wt. % to 20 wt. %, or at least 0.01 wt. %, or at least 0.1 wt. %, or at least 0.5 wt. %, or at least 1 wt. %, and up to 20 wt. %, or up to 15 wt. %, or up to 10 wt. %, or up to 8 wt. %, or up to 5 wt. % of an anti-aging active, based on the weight of the personal care composition. Examples of suitable ranges include a personal care composition comprising, in addition to a liphophilic hydroxytyrosol carbonate ester compound, an anti-aging active present in an amount of from 0.001 wt. % to 20 wt. %, or 0.001 wt. % to 15 wt. %, or 0.001 wt. % to 10 wt. %, or 0.001 wt. % to 8 wt. %, or 0.001 wt. % to 5 wt. %, or 0.01 wt. % to 20 wt. %, or 0.01 wt. % to 15 wt. %, or 0.01 wt. % to 10 wt. %, or 0.01 wt. % to 8 wt. %, or 0.01 wt. % to 5 wt. %, or 0.1 wt. % to 20 wt. %, or 0.1 wt. % to 15 wt. %, or 0.1 wt. % to 10 wt. %, or 0.1 wt. % to 8 wt. %, or 0.1 wt. % to 5 wt. %, or 0.5 wt. % to 20 wt. %, or 0.5 wt. % to 15 wt. %, or 0.5 wt. % to 10 wt. %, or 0.5 wt. % to 8 wt. %, or 0.5 wt. % to 5 wt. %, or 1 wt. % to 20 wt. %, or 1 wt. % to 15 wt. %, or 1 wt. % to 10 wt. %, or 1 wt. % to 8 wt. %, or 1 wt. % to 5 wt. %, in each case based on the weight of the personal care composition.

Antioxidants

The personal care compositions of the invention may include liphophilic hydroxytyrosol carbonate ester compounds and additional anti-oxidant, Examples of such additional antioxidants include acetyl cysteine, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCl, diamylhydroquinone, di-t-butylhydroquinone, dicetyl thiodipropionate, dioleyl tocopheryl rnethylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isoodyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfate, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiol actic acid, thlosalicylic acid, tocophereth-5, tocopheretn-10, tocophereth-12, tocophereth-18, tocophereth-50, tocophersolan, tocopheryi linoleate, tocopheryl nicotinate, tocopheryl succinate, and tris(nonylphenyl)phosphite.

The personal care composition may contain, in addition to the liphophilic hydroxytyrosol carbonate ester compounds, from 0.001 wt. % to 20 wt. %, or at least 0.01 wt. %, or at least 0.1 wt. %, or at least 0.5 wt. %, or at least 1 wt. %, and up to 20 wt. %, or up to 15 wt. %, or up to 10 wt. %, or up to 8 wt. %, or up to 5 wt. % of an anti-oxidant other than the lipophilic hydroxytyrosol carbonate ester compounds, based on the weight of the personal care composition. Examples of suitable ranges include a personal care composition comprising, in addition to a liphophilic hydroxytyrosol carbonate ester compound, an antioxidant, other than the lipophilic hydroxytyrosol carbonate ester compounds, present in an amount of from 0.001 wt. % to 20 wt. %, or 0.001 wt. % to 15 wt. %, or 0.001 wt. % to 10 wt. %, or 0.001 wt. % to 8 wt. %, or 0.001 wt. % to 5 wt. %, or 0.01 wt. % to 20 wt. %, or 0.01 wt. % to 15 wt. %, or 0.01 wt. % to 10 wt. %, or 0.01 wt. % to 8 wt. %, or 0.01 wt. % to 5 wt. %, or 0.1 wt. % to 20 wt. %, or 0.1 wt. % to 15 wt. %, or 0.1 wt. % to 10 wt. %, or 0.1 wt. % to 8 wt. %, or 0.1 wt. % to 5 wt. %, or 0.5 wt. % to 20 wt. %, or 0.5 wt. % to 15 wt. %, or 0.5 wt. % to 10 wt. %, or 0.5 wt. % to 8 wt. %, or 0.5 wt. % to 5 wt. %, or 1 wt. % to 20 wt. %, or 1 wt. % to 15 wt. %, or 1 wt. % to 10 wt. %, or 1 wt. % to 8 wt. %, or 1 wt. % to 5 wt. %, in each case based on the weight of the personal care composition.

Medicinal Compounds

The personal care compositions of the invention may include liphophilic hydroxytyrosol carbonate ester compounds and a medicinal compound. Examples of medicinal compounds include anti-irritants such as steroids and non-steroidal anti-inflammatories, anti-microbial agents, anti-acne agents, agents used to treat rosacea, analgesics, anesthetics, anorectals, antihistamines, antibiotics, antifungals, antivirals, anti-cancer actives, scabicides, pediculicides, antineoplastics, antiperspirants, antipruritics, antpsoriatic agents, antiseborrheic agents, biologically active proteins and peptides, burn treatment agents, cauterizing agents, depigmenting agents, depilatories, diaper rash treatment agents, enzymes, hair growth stimulants, hair growth retardants including DFMO and its salts and analogs, hernostatics, kerotolytics, canker sore treatment agents, cold sore treatment agents, dental and periodontal treatment agents, photosensitizing actives, skin protectantibarrier agents, steroids including hormones and corticosteroids, sunburn treatment agents, sunscreens, transdermal actives, nasal actives, vaginal actives, wart treatment agents, wound treatment agents, wound healing agents, and the like.

The personal care composition may contain, in addition to the liphophilic hydroxytyrosol carbonate ester compounds, from 0.001 wt. % to 20 wt. %, or at least 0.01 wt. %, or at least 0.1 wt. %, or at least 0.5 wt. %, or at least 1 wt. %, and up to 20 wt. %, or up to 15 wt. %, or up to 10 wt. %, or up to 8 wt. %, or up to 5 wt. % of a medicinal compound, based on the weight of the personal care composition. Examples of suitable ranges include a personal care composition comprising, in addition to a liphophilic hydroxytyrosol carbonate ester compound, a medicinal compound present in an amount of from 0.001 wt. % to 20 wt. %, or 0.001 wt. % to 15 wt. %, or 0.001 wt. % to 10 wt. %, or 0.001 wt. % to 8 wt. %, or 0.001 wt. % to 5 wt. %, or 0.01 wt. % to 20 wt. %, or 0.01 wt. % to 15 wt. %, or 0.01 wt. % to 10 wt. %, or 0.01 wt. % to 8 wt. %, or 0.01 wt. % to 5 wt. %, or 0.1 wt. % to 20 wt. %, or 0.1 wt. % to 15 wt. %, or 0.1 wt. % to 10 wt. %, or 0.1 wt. % to 8 wt. %, or 0.1 wt. % to 5 wt. %, or 0.5 wt. % to 20 wt. %, or 0.5 wt. % to 15 wt. %, or 0.5 wt. % to 10 wt. %, or 0.5 wt. % to 8 wt. %, or 0.5 wt. % to 5 wt. %, or 1 wt. % to 20 wt. %, or 1 wt. % to 15 wt. %, or 1 wt. % to 10 wt. %, or 1 wt. % to 8 wt. %, or 1 wt. % to 5 wt. %, in each case based on the weight of the personal care composition.

Vitamins

The personal care compositions of the invention may include liphophilic hydroxytyrosol carbonate ester compounds and a vitamin. Suitable vitamins include vitamins A, B, C, D, E, and K.

The personal care composition may contain, in addition to the liphophilic hydroxytyrosol carbonate ester compounds, from 0.001 wt. % to 20 wt. %, or at least 0.01 wt. %, or at least 0.1 wt. %, or at least 0.5 wt. %, or at least 1 wt. %, and up to 20 wt. %, or up to 15 wt. %, or up to 10 wt. %, or up to 8 wt. %, or up to 5 wt. % of a vitamin, based on the weight of the personal care composition. Examples of suitable ranges include a personal care composition comprising, in addition to a liphophilic hydroxytyrosol carbonate ester compound, a vitamin present in an amount of from 0.001 wt. % to 20 wt. %, or 0.001 wt. % to 15 wt. %, or 0.001 wt. % to 10 wt. %, or 0.001 wt. % to 8 wt. %, or 0.001 wt. % to 5 wt. %, or 0.01 wt. % to 20 wt. %, or 0.01 wt. % to 15 wt. %, or 0.01 wt. % to 10 wt. %, or 0.01 wt. % to 8 wt. %, or 0.01 wt. % to 5 wt. %, or 0.1 wt. % to 20 wt. %, or 0.1 wt. % to 15 wt. %, or 0.1 wt. % to 10 wt. %, or 0.1 wt. % to 8 wt. %, or 0.1 wt. % to 5 wt. %, or 0.5 wt. % to 20 wt. %, or 0.5 wt. % to 15 wt. %, or 0.5 wt. % to 10 wt. %, or 0.5 wt. % to 8 wt. %, or 0.5 wt. % to 5 wt. %, or 1 wt. % to 20 wt. %, or 1 wt. % to 15 wt. %, or 1 wt. % to 10 wt. %, or 1 wt. % to 8 wt. %, or 1 wt. % to 5 wt. %, in each case based on the weight of the personal care composition.

Sunscreen and Suntan Agents Including UV Absorbers

The personal care compositions of the invention may include liphophilic hydroxytyrosol carbonate ester compounds and a compound to sunscreen or suntan agents. Sunsreen agents scatter or absorb ultraviolet rays for the effect of blocking UV light as in the case, and suntan agents function to intensify the effect of UV light. Sunscreen compositions allow for a stable and prolonged period of protection from ultraviolet rays after topical application to skin. Examples of UV absorbing compounds include paraaminobenzoic acid (PABA), derivatives or salts of PABA such as PABA esters (glyceryl PABA, amyldimethyl PABA and octyldimethyl PABA), butyl PABA, ethyl PABA, ethyl dihydroxypropyl PABA; benzophenones (oxybenzone, sulisobenzone, benzophenone, and benzophenone-1 through 12 such as 2-hydroxy-4-methoxyphenyl)-phenylmethanone known as benzophenone-3), cinnamates (octyl methoxycinnamate, isoamyl p-methoxycinnamate, octylmethoxy cinnamate, diisopropyi methyl cinnamate, DEA-methoxycinnamate, ethyl diisopropylcinnamate, glyceryl octanoate dimethoxycinnamate, 2-ethoxyethyl p-methoxycinnamate known as cinoxate, and ethyl methoxycinnamate), cinnamate esters, salicylates (homomethyl salicylate, benzyl salicylate, glycol salicylate, triethanol salicylate, isopropylbenzyl salicylate, octyl aslicylate, etc.), anthranilates, ethyl urocanate, homosalate, octisalate, dibenzoylrnethane derivatives, octyl triazone, digalloy trioieate, glyceryl aminobenzoate, iawsone with dihydroxyacetone, ethyihexyl triazone, dioctyl butamido triazone, benzylidene malonate polysiloxane, terephthalylidene dicamphor sulfonic acid, disodium phenyl dibenzimidazole tetrasulfonate, phenylbenzimidazole sulfonic acid, diethylamino hydroxybenzoyl hexyl benzoate, bis diethylamino hydroxybenzoyl benzoate, bis benzoxazoylphenyl ethylhexylimino triazine, drometrizole trisiloxane, methylene bis-benzotriazolyl tetramethylbutylphenol, and bis-ethylhexyloxyphenol methoxyphenyltriazine, 4-methylbenzylidenecamphor, isopentyl 4-methoxycinnamate, 2-ethylhexyl 2-hydroxybenzoate (also known as octisalate); 2-ethylhexyl 2-cyano-3,3-diphenyl-2-propenoate (also known as octocrylene), 1-(4-methoxyphenyl)-3-(4-tert-butylphenyl)propane-1,3-dione (also known as avobenzone), 2-hydroxyl-4-methoxybenzophenone-5-sulfonic acid, 1-(4-methoxyphenyl)-3-(4-tert-butylphenyl)propane-1,3-dione, and terephthalylidene dicamphor sulfonic acid also known as ecamsule. Non-limiting examples of physical sunblocks include, kaolin, talc, petrolatum and metal oxides (e.g., titanium dioxide and zinc oxide and combinations thereof). The sunscreen agent may contain compounds that both scatter and absorb uv light such as Tinosorb M, especially those particles of Tinosorb M having an average particle size below 200 nm. The personal care compositions can have UVA and UVB absorption properties. The compositions can have an sun protection factor (SPF) of 2, 3, 4, 5, 6, 7, 8, 9, 10, 11, 12, 13, 14, 15, 20, 25, 30, 35, 40, 45, 50, 55, 60, 70, 80, 90 or more, or any integer or derivative therein.

The personal care composition may contain, in addition to the liphophilic hydroxytyrosol carbonate ester compounds, from 0.001 wt. % to 20 wt. %, or at least 0.01 wt. %, or at least 0.1 wt. %, or at least 0.5 wt. %, or at least 1 wt. %, and up to 20 wt. %, or up to 15 wt. %, or up to 10 wt. %, or up to 8 wt. %, or up to 5 wt. % of a sunscreen agent, based on the weight of the personal care composition. Examples of suitable ranges include a personal care composition comprising, in addition to a liphophilic hydroxytyrosol carbonate ester compound, a sunscreen agent present in an amount of from 0.001 wt. % to 20 wt. %, or 0.001 wt. % to 15 wt. %, or 0.001 wt. % to 10 wt. %, or 0.001 wt. % to 8 wt. %, or 0.001 wt. % to 5 wt. %, or 0.01 wt. % to 20 wt. %, or 0.01 wt. % to 15 wt. %, or 0.01 wt. % to 10 wt. %, or 0.01 wt. % to 8 wt. %, or 0.01 wt. % to 5 wt. %, or 0.1 wt. % to 20 wt. %, or 0.1 wt. % to 15 wt. %, or 0.1 wt. % to 10 wt. %, or 0.1 wt. % to 8 wt. %, or 0.1 wt. % to 5 wt. %, or 0.5 wt. % to 20 wt. %, or 0.5 wt. % to 15 wt. %, or 0.5 wt. % to 10 wt. %, or 0.5 wt. % to 8 wt. %, or 0.5 wt. % to 5 wt. %, or 1 wt. % to 20 wt. %, or 1 wt. % to 15 wt. %, or 1 wt. % to 10 wt. %, or 1 wt. % to 8 wt. %, or 1 wt. % to 5 wt. %, in each case based on the weight of the personal care composition.

The personal care composition may contain, in addition to the liphophilic hydroxytyrosol carbonate ester compounds, from 0.001 wt. % to 20 wt. %, or at least 0.01 wt. %, or at least 0.1 wt. %, or at least 0.5 wt. %, or at least 1 wt. %, and up to 20 wt. %, or up to 15 wt. %, or up to 10 wt. %, or up to 8 wt. %, or up to 5 wt. % of a suntanning agent, based on the weight of the personal care composition. Examples of suitable ranges include a personal care composition comprising, in addition to a liphophilic hydroxytyrosol carbonate ester compound, a suntanning agent present in an amount of from 0.001 wt. % to 20 wt. %, or 0.001 wt. % to 15 wt. %, or 0.001 wt. % to 10 wt. %, or 0.001 wt. % to 8 wt. %, or 0.001 wt. % to 5 wt. %, or 0.01 wt. % to 20 wt. %, or 0.01 wt. % to 15 wt. %, or 0.01 wt. % to 10 wt. %, or 0.01 wt. % to 8 wt. %, or 0.01 wt. % to 5 wt. %, or 0.1 wt. % to 20 wt. %, or 0.1 wt. % to 15 wt. %, or 0.1 wt. % to 10 wt. %, or 0.1 wt. % to 8 wt. %, or 0.1 wt. % to 5 wt. %, or 0.5 wt. % to 20 wt. %, or 0.5 wt. % to 15 wt. %, or 0.5 wt. % to 10 wt. %, or 0.5 wt. % to 8 wt. %, or 0.5 wt. % to 5 wt. %, or 1 wt. % to 20 wt. %, or 1 wt. % to 15 wt. %, or 1 wt. % to 10 wt. %, or 1 wt. % to 8 wt. %, or 1 wt. % to 5 wt. %, in each case based on the weight of the personal care composition.

Skin Bleaching Agents

The personal care compositions of the invention may include liphophilic hydroxytyrosol carbonate ester compounds and a skin bleaching agent Examples of skin bleaching agents include hydroquinone and niacinamide lactate.

The personal care composition may contain, in addition to the liphophilic hydroxytyrosol carbonate ester compounds, from 0.001 wt. % to 20 wt. %, or at least 0.01 wt. %, or at least 0.1 wt. %, or at least 0.5 wt. %, or at least 1 wt. %, and up to 20 wt. %, or up to 15 wt. %, or up to 10 wt. %, or up to 8 wt. %, or up to 5 wt. % of skin bleaching agent, based on the weight of the personal care composition. Examples of suitable ranges include a personal care composition comprising, in addition to a liphophilic hydroxytyrosol carbonate ester compound, a skin bleaching agent present in an amount of from 0.001 wt. % to 20 wt. %, or 0.001 wt. % to 15 wt. %, or 0.001 wt. % to 10 wt. %, or 0.001 wt. % to 8 wt. %, or 0.001 wt. % to 5 wt. %, or 0.01 wt. % to 20 wt. %, or 0.01 wt. % to 15 wt. %, or 0.01 wt. % to 10 wt. %, or 0.01 wt. % to 8 wt. %, or 0.01 wt. % to 5 wt. %, or 0.1 wt. % to 20 wt. %, or 0.1 wt. % to 15 wt. %, or 0.1 wt. % to 10 wt. %, or 0.1 wt. % to 8 wt. %, or 0.1 wt. % to 5 wt. %, or 0.5 wt. % to 20 wt. %, or 0.5 wt. % to 15 wt. %, or 0.5 wt. % to 10 wt. %, or 0.5 wt. % to 8 wt. %, or 0.5 wt. % to 5 wt. %, or 1 wt. % to 20 wt. %, or 1 wt. % to 15 wt. %, or 1 wt. % to 10 wt. %, or 1 wt. % to 8 wt. %, or 1 wt. % to 5 wt. %, in each case based on the weight of the personal care composition.

Anti-Acne Agents

The personal care compositions of the invention may include liphophilic hydroxytyrosol carbonate ester compounds and an anti-acne agent. Examples of suitable anti-acne agents include benzoyl peroxide, salicylic acid, retinoic acid (tretinoin), isotretinoin, retinol, adapalene, tazarotene, and azelaic acid.

The personal care composition may contain, in addition to the liphophilic hydroxytyrosol carbonate ester compounds, from 0.001 wt. % to 20 wt. %, or at least 0.01 wt. %, or at least 0.1 wt. %, or at least 0.5 wt. %, or at least 1 wt. %, and up to 20 wt. %, or up to 15 wt. %, or up to 10 wt. %, or up to 8 wt. %, or up to 5 wt. % of an anti-acne agent, based on the weight of the personal care composition. Examples of suitable ranges include a personal care composition comprising, in addition to a liphophilic hydroxytyrosol carbonate ester compound, an anti-acne agent present in an amount of from 0.001 wt. % to 20 wt. %, or 0.001 wt. % to 15 wt. %, or 0.001 wt. % to 10 wt. %, or 0.001 wt. % to 8 wt. %, or 0.001 wt. % to 5 wt. %, or 0.01 wt. % to 20 wt. %, or 0.01 wt. % to 15 wt. %, or 0.01 wt. % to 10 wt. %, or 0.01 wt. % to 8 wt. %, or 0.01 wt. % to 5 wt. %, or 0.1 wt. % to 20 wt. %, or 0.1 wt. % to 15 wt. %, or 0.1 wt. % to 10 wt. %, or 0.1 wt. % to 8 wt. %, or 0.1 wt. % to 5 wt. %, or 0.5 wt. % to 20 wt. %, or 0.5 wt. % to 15 wt. %, or 0.5 wt. % to 10 wt. %, or 0.5 wt. % to 8 wt. %, or 0.5 wt. % to 5 wt. %, or 1 wt. % to 20 wt. %, or 1 wt. % to 15 wt. %, or 1 wt. % to 10 wt. %, or 1 wt. % to 8 wt. %, or 1 wt. % to 5 wt. %, in each case based on the weight of the personal care composition.

Botanical Extracts and Essential Oils

The personal care compositions of the invention may include liphophilic hydroxytyrosol carbonate ester compounds and a botanical extract and/or essential oils. These are derived from herbs, flowers, trees, and other plants. Such oils and extracts are typically present as tiny droplets between the plant's cells, and can be extracted by several method known to those of skill in the art (e.g., steam distilled, enfleurage (i.e., extraction by using fat), maceration, solvent extraction, or mechanical pressing). Essential oils are insoluble in water and are soluble in alcohol, ether, fixed oils (vegetal), and other organic solvents. Extracts can be water soluble and soluble in alcohol or oils. Typical physical characteristics found in essential oils include boiling points that vary from about 160° to 240° C. and densities ranging from about 0.759 to about 1.096.

Essential oils typically are named by the plant from which the oil is found. For example, rose oil or peppermint oil are derived from rose or peppermint plants, respectively. Examples of essential oils and extracts that can be used include the oils or extracts of sesame, macadamia nut, tea tree, evening primrose, aloe vera, Spanish sage, Spanish rosemary, coriander, thyme, pimento berries, rose, anise, balsam, bergamot, rosewood, cedar, chamomile, sage, clary sage, clove, cypress, eucalyptus, fennel, cucumber, sea fennel, ginseng, frankincense, geranium, ginger, grapefruit, jasmine, juniper, lavender, lemon, lemongrass, lime, mandarin, marjoram, myrrh, ginkgo biloba, neroli, orange, patchouli, pepper, black pepper, petitgrain, pine, rose otto, rosemary, sandalwood, spearmint, spikenard, vetiver, wintergreen, or ylang ylang.

The personal care composition may contain, in addition to the liphophilic hydroxytyrosol carbonate ester compounds, from 0.001 wt. % to 20 wt. %, or at least 0.01 wt. %, or at least 0.1 wt. %, or at least 0.5 wt. %, or at least 1 wt. %, and up to 20 wt. %, or up to 15 wt. %, or up to 10 wt. %, or up to 8 wt. %, or up to 5 wt. % of a botanical extract or essential oil, based on the weight of the personal care composition. Examples of suitable ranges include a personal care composition comprising, in addition to a liphophilic hydroxytyrosol carbonate ester compound, a botanical extract or essential oil present in an amount of from 0.001 wt. % to 20 wt. %, or 0.001 wt. % to 15 wt. %, or 0.001 wt. % to 10 wt. %, or 0.001 wt. % to 8 wt. %, or 0.001 wt. % to 5 wt. %, or 0.01 wt. % to 20 wt. %, or 0.01 wt. % to 15 wt. %, or 0.01 wt. % to 10 wt. %, or 0.01 wt. % to 8 wt. %, or 0.01 wt. % to 5 wt. %, or 0.1 wt. % to 20 wt. %, or 0.1 wt. % to 15 wt. %, or 0.1 wt. % to 10 wt. %, or 0.1 wt. % to 8 wt. %, or 0.1 wt. % to 5 wt. %, or 0.5 wt. % to 20 wt. %, or 0.5 wt. % to 15 wt. %, or 0.5 wt. % to 10 wt. %, or 0.5 wt. % to 8 wt. %, or 0.5 wt. % to 5 wt. %, or 1 wt. % to 20 wt. %, or 1 wt. % to 15 wt. %, or 1 wt. % to 10 wt. %, or 1 wt. % to 8 wt. %, or 1 wt. % to 5 wt. %, in each case based on the weight of the personal care composition.

Adhesion Promoters

The personal care compositions of the invention may include liphophilic hydroxytyrosol carbonate ester compounds and an adhesion promoter. Examples of suitable adhesion promoters include polymethyl methacrylate, hydroxyiated lanolin, copolymer of methyl vinyl etherimaleic anhydride, sulfopolyesters, sucrose acetate isobutyrate, calcium/sodium PVM/MA copolymer, polyvinylpyrrolidone, hydrogenated polyisobutene, hydrogenated rosinate, and acrylate copolymers The personal care composition may contain, in addition to the liphophilic hydroxytyrosol carbonate ester compounds, from 0.001 wt. % to 20 wt. %, or at least 0.01 wt. %, or at least 0.1 wt. %, or at least 0.5 wt. %, or at least 1 wt. %, and up to 20 wt. %, or up to 15 wt. %, or up to 10 wt. %, or up to 8 wt. %, or up to 5 wt. % of an adhesion promoter, based on the weight of the personal care composition. Examples of suitable ranges include a personal care composition comprising, in addition to a liphophilic hydroxytyrosol carbonate ester compound, an adhesion promoter present in an amount of from 0.001 wt. % to 20 wt. %, or 0.001 wt. % to 15 wt. %, or 0.001 wt. % to 10 wt. %, or 0.001 wt. % to 8 wt. %, or 0.001 wt. % to 5 wt. %, or 0.01 wt. % to 20 wt. %, or 0.01 wt. % to 15 wt. %, or 0.01 wt. % to 10 wt. %, or 0.01 wt. % to 8 wt. %, or 0.01 wt. % to 5 wt. %, or 0.1 wt. % to 20 wt. %, or 0.1 wt. % to 15 wt. %, or 0.1 wt. % to 10 wt. %, or 0.1 wt. % to 8 wt. %, or 0.1 wt. % to 5 wt. %, or 0.5 wt. % to 20 wt. %, or 0.5 wt. % to 15 wt. %, or 0.5 wt. % to 10 wt. %, or 0.5 wt. % to 8 wt. %, or 0.5 wt. % to 5 wt. %, or 1 wt. % to 20 wt. %, or 1 wt. % to 15 wt. %, or 1 wt. % to 10 wt. %, or 1 wt. % to 8 wt. %, or 1 wt. % to 5 wt. %, in each case based on the weight of the personal care composition.

Plasticizers

The personal care compositions of the invention may include liphophilic hydroxytyrosol carbonate ester compounds and a plasticizer. Examples of suitable plasticizers include camphor, diethylene glycol dibenzoate, diethyl phthalate, ethyl tosylamide, neopentyl glycol, octanediol, styrenelacrylates copolymer/polyurethane, sucrose acetate isobutyrate, tricetyl phosphate, butyl phthalimide, triacetin, epoxidized soybean oil, dibutyl phthalate, diethyl succinate, dimethyl phthalate, Arabic gum, carrageenan gum, karaya gum, tragacanth gum, guar gum, locust gum, bean gum; quince seed (*cydonia oblonga*), casein, dextrine, gelatine, sodium pectate, sodium alginate, methylcellulose, CMC, hydroxyethylcellulose, hydroxypropylcellulose, PVA, PVM, PVP, sodium poiyacrylate, carboxyvinylpolymer, locust bean gum, tamarind gum, dialkyldimethylammonium cellulose sulfate, xanthan gum, aluminium magnesium silicate, bentonite,hectorite, aluminium magnesium silicate (veegum), laponite, silicic anhydride, citrate ester, a sebacate, a glycol, an adipate, a phthalate, a phosphate, mineral oil, trolamine, triacetin, or a phospholipid. Examples of a citrate ester include isopropyl citrate, triethyl citrate (TEC), acetyl triethyl citrate (ATEC), acetyl trihexyl citrate (ATHC), tributyl citrate (TBC), and acetyl tributyl citrate (ATBC). Examples of sebacate include dibutyl sebacate and diethyl sebacate.

The personal care composition may contain, in addition to the liphophilic hydroxytyrosol carbonate ester compounds, from 0.001 wt. % to 20 wt. %, or at least 0.01 wt. %, or at least 0.1 wt. %, or at least 0.5 wt. %, or at least 1 wt. %, and up to 20 wt. %, or up to 15 wt. %, or up to 10 wt. %, or up to 8 wt. %, or up to 5 wt. % of a plasticizer, based on the weight of the personal care composition. Examples of suitable ranges include a personal care composition comprising, in addition to a liphophilic hydroxytyrosol carbonate ester compound, a plasticizer present in an amount of from 0.001 wt. % to 20 wt. %, or 0.001 wt. % to 15 wt. %, or 0.001 wt. % to 10 wt. %, or 0.001 wt. % to 8 wt. %, or 0.001 wt. % to 5 wt. %, or 0.01 wt. % to 20 wt. %, or 0.01 wt. % to 15 wt. %, or 0.01 wt. % to 10 wt. %, or 0.01 wt. % to 8 wt. %, or 0.01 wt. % to 5 wt. %, or 0.1 wt. % to 20 wt. %, or 0.1 wt. % to 15 wt. %, or 0.1 wt. % to 10 wt. %, or 0.1 wt. % to 8 wt. %, or 0.1 wt. % to 5 wt. %, or 0.5 wt. % to 20 wt. %, or 0.5 wt. % to 15 wt. %, or 0.5 wt. % to 10 wt. %, or 0.5 wt. % to 8 wt. %, or 0.5 wt. % to 5 wt. %, or 1 wt. % to 20 wt. %, or 1 wt. % to 15 wt. %, or 1 wt. % to 10 wt. %, or 1 wt. % to 8 wt. %, or 1 wt. % to 5 wt. %, in each case based on the weight of the personal care composition.

Film Formers

The personal care compositions of the invention may include liphophilic hydroxytyrosol carbonate ester compounds and a film former. Examples of suitable film formers include copolymer of methyl vinyl etherimaleic anhydride, sulfopolyesters, sucrose acetate isobutyrate. calcium/sodium PVM/MA copolymer, polyvinylpyrrolidone, hydrogenated polyisobutene, hydrogenated rosinate, and acrylate copolymers.

The personal care composition may contain, in addition to the liphophilic hydroxytyrosol carbonate ester compounds, from 0.001 wt. % to 20 wt. %, or at least 0.01 wt. %, or at least 0.1 wt. %, or at least 0.5 wt. %, or at least 1 wt. %, and up to 20 wt. %, or up to 15 wt. %, or up to 10 wt. %, or up to 8 wt. %, or up to 5 wt. % of a film former, based on the weight of the personal care composition. Examples of suitable ranges include a personal care composition comprising, in addition to a liphophilic hydroxytyrosol carbonate ester compound, a film forming agent present in an amount of from 0.001 wt. % to 20 wt. %, or 0.001 wt. % to 15 wt. %, or 0.001 wt. % to 10 wt. %, or 0.001 wt. % to 8 wt. %, or 0.001 wt. % to 5 wt. %, or 0.01 wt. % to 20 wt. %, or 0.01 wt. % to 15 wt. %, or 0.01 wt. % to 10 wt. %, or 0.01 wt. % to 8 wt. %, or 0.01 wt. % to 5 wt. %, or 0.1 wt. % to 20 wt. %, or 0.1 wt. % to 15 wt. %, or 0.1 wt. % to 10 wt. %, or 0.1 wt. % to 8 wt. %, or 0.1 wt. % to 5 wt. %, or 0.5 wt. % to 20 wt. %, or 0.5 wt. % to 15 wt. %, or 0.5 wt. % to 10 wt. %, or 0.5 wt. % to 8 wt. %, or 0.5 wt. % to 5 wt. %, or 1 wt. % to 20 wt. %, or 1 wt. % to 15 wt. %, or 1 wt. % to 10 wt. %, or 1 wt. % to 8 wt. %, or 1 wt. % to 5 wt. %, in each case based on the weight of the personal care composition.

Hair Fixatives

The personal care compositions of the invention may include liphophilic hydroxytyrosol carbonate ester compounds and a hair fixative. Examples of suitable hair fixatives include sulfopolyesters, polyacrylamide, polyvinyl acetate, polyvinyl butyral, polyvinylpyrrolidone, trimethylpropane triacrylate, VP/VA Copolymer, chitosan, and polyacrylates.

The personal care composition may contain, in addition to the liphophilic hydroxytyrosol carbonate ester compounds, from 0.001 wt. % to 20 wt. %, or at least 0.01 wt. %, or at least 0.1 wt. %, or at least 0.5 wt. %, or at least 1 wt. %, and up to 20 wt. %, or up to 15 wt. %, or up to 10 wt. %, or up to 8 wt. %, or up to 5 wt. % of a hair fixative, based on the weight of the personal care composition. Examples of suitable ranges include a personal care composition comprising, in addition to a liphophilic hydroxytyrosol carbonate ester compound, a hair fixative present in an amount of from 0.001 wt. % to 20 wt. %, or 0.001 wt. % to 15 wt. %, or 0.001 wt. % to 10 wt. %, or 0.001 wt. % to 8 wt. %, or 0.001 wt. % to 5 wt. %, or 0.01 wt. % to 20 wt. %, or 0.01 wt. % to 15 wt. %, or 0.01 wt. % to 10 wt. %, or 0.01 wt. % to 8 wt. %, or 0.01 wt. % to 5 wt. %, or 0.1 wt. % to 20 wt. %, or 0.1 wt. % to 15 wt. %, or 0.1 wt. % to 10 wt. %, or 0.1 wt. % to 8 wt. %, or 0.1 wt. % to 5 wt. %, or 0.5 wt. % to 20 wt. %, or 0.5 wt. % to 15 wt. %, or 0.5 wt. % to 10 wt. %, or 0.5 wt. % to 8 wt. %, or 0.5 wt. % to 5 wt. %, or 1 wt. % to 20 wt. %, or 1 wt. % to 15 wt. %, or 1 wt. % to 10 wt. %, or 1 wt. % to 8 wt. %, or 1 wt. % to 5 wt. %, in each case based on the weight of the personal care composition.

Thickening Agents

The personal care compositions of the invention may include liphophilic hydroxytyrosol carbonate ester compounds and a thickening agent to increase the viscosity of the personal care composition. Examples of thickening agents include carboxylic acid polymers, crosslinked polyacrylate polymers, polyacrylamide polymers, polysaccharides, and gums. Examples of crosslinked polyacrylate polymers include cationic and nonionic polymers. Examples of polyacrylamide polymers (including nonionic polyacrylamide polymers including substituted branched or unbranched polymers) include polyacrylamide, isoparaffin and laureth-7, multi-block copolymers of acrylamides and substituted acrylamides with acrylic acids and substituted acrylic acids. Examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (preferably hydroxy ethylated or hydroxypropylated) to form a hydroxyalkylated cellulose which is then further modified with a $C_{10}$-$C_{30}$ straight chain or branched chain alkyl group through an ether linkage. Typically these polymers are ethers of $C_{10}$-$C_{30}$ straight or branched chain alcohols with hydroxyalkylcelluloses. Other useful polysaccharides include scleroglucans comprising a linear chain of (1-3) linked glucose units with a (1-6) linked glucose every three unit. Examples of gums include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboyxmethyl dextran, sodium carrageenan, tragacanth gum, xanthan gum, and mixtures thereof.

The personal care composition may contain, in addition to the liphophilic hydroxytyrosol carbonate ester compounds, from 0.001 wt. % to 20 wt. %, or at least 0.01 wt. %, or at least 0.1 wt. %, or at least 0.5 wt. %, or at least 1 wt. %, and up to 20 wt. %, or up to 15 wt. %, or up to 10 wt. %, or up to 8 wt. %, or up to 5 wt. % of a thickener, based on the weight of the personal care composition. Examples of suitable ranges include a personal care composition comprising, in addition to a liphophilic hydroxytyrosol carbonate ester compound, a thickener present in an amount of from 0.001 wt. % to 20 wt. %, or 0.001 wt. % to 15 wt. %, or 0.001 wt. % to 10 wt. %, or 0.001 wt. % to 8 wt. %, or 0.001 wt. % to 5 wt. %, or 0.01 wt. % to 20 wt. %, or 0.01 wt. % to 15 wt. %, or 0.01 wt. % to 10 wt. %, or 0.01 wt. % to 8 wt. %, or 0.01 wt. % to 5 wt. %, or 0.1 wt. % to 20 wt. %, or 0.1 wt. % to 15 wt. %, or 0.1 wt. % to 10 wt. %, or 0.1 wt. % to 8 wt. %, or 0.1 wt. % to 5 wt. %, or 0.5 wt. % to 20 wt. %, or 0.5 wt. % to 15 wt. %, or 0.5 wt. % to 10 wt. %, or 0.5 wt. % to 8 wt. %, or 0.5 wt. % to 5 wt. %, or 1 wt. % to 20 wt. %, or 1 wt. % to 15 wt. %, or 1 wt. % to 10 wt. %, or 1 wt. % to 8 wt. %, or 1 wt. % to 5 wt. %, in each case based on the weight of the personal care composition.

Solvents

The personal care compositions of the invention may include liphophilic hydroxytyrosol carbonate ester compounds and a solvent. Solvents act to dissolve or disperse by solvating actions. Examples of suitable solvents include oils and water.

The personal care composition may contain, in addition to the liphophilic hydroxytyrosol carbonate ester compounds, from 0.001 wt. % to 20 wt. %, or at least 0.01 wt. %, or at least 0.1 wt. %, or at least 0.5 wt. %, or at least 1 wt. %, and up to 20 wt. %, or up to 15 wt. %, or up to 10 wt. %, or up to 8 wt. %, or up to 5 wt. % of a solvent based on the weight of the personal care composition. Examples of suitable ranges include a personal care composition comprising, in addition to a liphophilic hydroxytyrosol carbonate ester compound, a solvent present in an amount of from 0.001 wt. % to 20 wt. %, or 0.001 wt. % to 15 wt. %, or 0.001 wt. % to 10 wt. %, or 0.001 wt. % to 8 wt. %, or 0.001 wt. % to 5 wt. %, or 0.01 wt. % to 20 wt. %, or 0.01 wt. % to 15 wt. %, or 0.01 wt. % to 10 wt. %, or 0.01 wt. % to 8 wt. %, or 0.01 wt. % to 5 wt. %, or 0.1 wt. % to 20 wt. %, or 0.1 wt. % to 15 wt. %, or 0.1 wt. % to 10 wt. %, or 0.1 wt. % to 8 wt. %, or 0.1 wt. % to 5 wt. %, or 0.5 wt. % to 20 wt. %, or 0.5 wt. % to 15 wt. %, or 0.5 wt. % to 10 wt. %, or 0.5 wt. % to 8 wt. %, or 0.5 wt. % to 5 wt. %, or 1 wt. % to 20 wt. %, or 1 wt. % to 15 wt. %, or 1 wt. % to 10 wt. %, or 1 wt. % to 8 wt. %, or 1 wt. % to 5 wt. %, in each case based on the weight of the personal care composition.

Propellants

The personal care compositions of the invention may include liphophilic hydroxytyrosol carbonate ester compounds and a propellant. Examples of suitable propellants include isobutane, propane, butane, hydrofluorocarbon, ethane, isopentane, hydrochlorofluorocarbon, and dimethyl carbonate.

The personal care composition may contain, in addition to the liphophilic hydroxytyrosol carbonate ester compounds, from 0.001 wt. % to 20 wt. %, or at least 0.01 wt. %, or at least 0.1 wt. %, or at least 0.5 wt. %, or at least 1 wt. %, and up to 20 wt. %, or up to 15 wt. %, or up to 10 wt. %, or up to 8 wt. %, or up to 5 wt. % of a propellant, based on the weight of the personal care composition. Examples of suitable ranges include a personal care composition comprising, in addition to a liphophilic hydroxytyrosol carbonate ester compound, a propellant present in an amount of from 0.001 wt. % to 20 wt. %, or 0.001 wt. % to 15 wt. %, or 0.001 wt. % to 10 wt. %, or 0.001 wt. % to 8 wt. %, or 0.001 wt. % to 5 wt. %, or 0.01 wt. % to 20 wt. %, or 0.01 wt. % to 15 wt. %, or 0.01 wt. % to 10 wt. %, or 0.01 wt. % to 8 wt. %, or 0.01 wt. % to 5 wt. %, or 0.1 wt. % to 20 wt. %, or 0.1 wt. % to 15 wt. %, or 0.1 wt. % to 10 wt. %, or 0.1 wt. % to 8 wt. %, or 0.1 wt. % to 5 wt. %, or 0.5 wt. % to 20 wt. %, or 0.5 wt. % to 15 wt. %, or 0.5 wt. % to 10 wt. %, or 0.5 wt. % to 8 wt. %, or 0.5 wt. % to 5 wt. %, or 1 wt. % to 20 wt. %, or 1 wt. % to 15 wt. %, or 1 wt. % to 10 wt. %, or 1 wt. % to 8 wt. %, or 1 wt. % to 5 wt. %, in each case based on the weight of the personal care composition.

Colorants: Pigments and Dyes

The personal care compositions of the invention may include liphophilic hydroxytyrosol carbonate ester compounds and a colorant (e.g. pigment or dye). Examples of suitable colorants include dyes such as Blue 1, Blue 1 Lake, Red 40, D&C blue no. 4. D&C green no. 5, D&C orange no. 4, D&C red no. 17, D&C red no. 33, D&C violet no. 2, D&C yellow no. 10, and D&C yellow no. 11; the mineral pigments such as zinc oxide, titanium dioxide, optionally surface treated, zirconium oxide, cerium oxide, iron oxide (black, yellow or red), chromium oxide, manganese violet, ultramarine blue, chromium hydrate and ferric blue; the organic pigments including carbon black, organic lake pigments of barium, strontium, calcium or aluminium, including those certified by the U.S. Food and Drug Administration (FDA) (examples D&C or FD&C) and those exempt from FDA certification, such as lakes based on cochineal carmine; and the nacreous pigments, and the azo, triphenylmethane, indigo, anthraquinone, and xanthine dyes. The pigments can also be spherical light scattering agents such as calcium aluminum borosilicate, PMMA, polyethylene, polystyrene, methyl methacrylate crosspolymer, nylon-12, ethylene/ acrylic acid copolymer, boron nitride, teflon, or silica.

The personal care composition may contain, in addition to the liphophilic hydroxytyrosol carbonate ester compounds, from 0.001 wt. % to 20 wt. %, or at least 0.01 wt. %, or at least 0.1 wt. %, or at least 0.5 wt. %, or at least 1 wt. %, and up to 20 wt. %, or up to 15 wt. %, or up to 10 wt. %, or up to 8 wt. %, or up to 5 wt. % of a colorant, based on the weight of the personal care composition. Examples of suitable ranges include a personal care composition comprising, in addition to a liphophilic hydroxytyrosol carbonate ester compound, a colorant present in an amount of from 0.001 wt. % to 20 wt. %, or 0.001 wt. % to 15 wt. %, or 0.001 wt. % to 10 wt. %, or 0.001 wt. % to 8 wt. %, or 0.001 wt. % to 5 wt. %, or 0.01 wt. % to 20 wt. %, or 0.01 wt. % to 15 wt. %, or 0.01 wt. % to 10 wt. %, or 0.01 wt. % to 8 wt. %, or 0.01 wt. % to 5 wt. %, or 0.1 wt. % to 20 wt. %, or 0.1 wt. % to 15 wt. %, or 0.1 wt. % to 10 wt. %, or 0.1 wt. % to 8 wt. %, or 0.1 wt. % to 5 wt. %, or 0.5 wt. % to 20 wt. %, or 0.5 wt. % to 15 wt. %, or 0.5 wt. % to 10 wt. %, or 0.5 wt. % to 8 wt. %, or 0.5 wt. % to 5 wt. %, or 1 wt. % to 20 wt. %, or 1 wt. % to 15 wt. %, or 1 wt. % to 10 wt. %, or 1 wt. % to 8 wt. %, or 1 wt. % to 5 wt. %, in each case based on the weight of the personal care composition.

Chelating Agents

The personal care compositions of the invention can include liphophilic hydroxytyrosol carbonate ester compounds and chelating agents, Examples of chelating agents include ethylenediamine tetracetic acid (EDTA) and their salts, including disodium EDTA and tetrasodium EDTA.

The personal care composition may contain, in addition to the liphophilic hydroxytyrosol carbonate ester compounds, from 0.001 wt. % to 20 wt. %, or at least 0.01 wt. %, or at least 0.1 wt. %, or at least 0.5 wt. %, or at least 1 wt. %, and up to 20 wt. %, or up to 15 wt. %, or up to 10 wt. %, or up to 8 wt. %, or up to 5 wt. % of a chelating agent, based on the weight of the personal care composition. Examples of suitable ranges include a personal care composition comprising, in addition to a liphophilic hydroxytyrosol carbonate ester compound, a chelating agent present in an amount of from 0.001 wt. % to 20 wt. %, or 0.001 wt. % to 15 wt. %, or 0.001 wt. % to 10 wt. %, or 0.001 wt. % to 8 wt. %, or 0.001 wt. % to 5 wt. %, or 0.01 wt. % to 20 wt. %, or 0.01 wt. % to 15 wt. %, or 0.01 wt. % to 10 wt. %, or 0.01 wt. % to 8 wt. %, or 0.01 wt. % to 5 wt. %, or 0.1 wt. % to 20 wt. %, or 0.1 wt. % to 15 wt. %, or 0.1 wt. % to 10 wt. %, or 0.1 wt. % to 8 wt. %, or 0.1 wt. % to 5 wt. %, or 0.5 wt. % to 20 wt. %, or 0.5 wt. % to 15 wt. %, or 0.5 wt. % to 10 wt. %, or 0.5 wt. % to 8 wt. %, or 0.5 wt. % to 5 wt. %, or 1 wt. % to 20 wt. %, or 1 wt. % to 15 wt. %, or 1 wt. % to 10 wt. %, or 1 wt. % to 8 wt. %, or 1 wt. % to 5 wt. %, in each case based on the weight of the personal care composition.

Absorbents and Adsorbents

The personal care compositions of the invention can include liphophilic hydroxytyrosol carbonate ester compounds and an absorbent compound. Examples of absorbent compounds include aluminum starch octenylsuccinate, kaolin, corn starch, oat starch, cyclodextrin, talc, and zeolites.

The personal care composition may contain, in addition to the liphophilic hydroxytyrosol carbonate ester compounds, from 0.001 wt. % to 20 wt. %, or at least 0.01 wt. %, or at least 0.1 wt. %, or at least 0.5 wt. %, or at least 1 wt. %, and up to 20 wt. %, or up to 15 wt. %, or up to 10 wt. %, or up to 8 wt. %, or up to 5 wt. % of an absorbent or adsorbent, based on the weight of the personal care composition. Examples of suitable ranges include a personal care composition comprising, in addition to a liphophilic hydroxytyrosol carbonate ester compound, an absorbent or adsorbent present in an amount of from 0.001 wt. % to 20 wt. %, or 0.001 wt. % to 15 wt. %, or 0.001 wt. % to 10 wt. %, or 0.001 wt. % to 8 wt. %, or 0.001 wt. % to 5 wt. %, or 0.01 wt. % to 20 wt. %, or 0.01 wt. % to 15 wt. %, or 0.01 wt. % to 10 wt. %, or 0.01 wt. % to 8 wt. %, or 0.01 wt. % to 5 wt. %, or 0.1 wt. % to 20 wt. %, or 0.1 wt. % to 15 wt. %, or 0.1 wt. % to 10 wt. %, or 0.1 wt. % to 8 wt. %, or 0.1 wt. % to 5 wt. %, or 0.5 wt. % to 20 wt. %, or 0.5 wt. % to 15 wt. %, or 0.5 wt. % to 10 wt. %, or 0.5 wt. % to 8 wt. %, or 0.5 wt. % to 5 wt. %, or 1 wt. % to 20 wt. %, or 1 wt. % to 15 wt. %, or 1 wt. % to 10 wt. %, or 1 wt. % to 8 wt. %, or 1 wt. % to 5 wt. %, in each case based on the weight of the personal care composition.

Humectant

The personal care composition of the invention can include liphophilic hydroxytyrosol carbonate ester compounds and a humectant. Examples of humectants include propylene glycol, butylene glycol, pentylene glycol, hexylene glycol, glyceryl triacetate, glycerol, xylitol, maltitol, manitol, sorbitol, polydextrose, quillaia, lactic acid, urea, and polyvinyl alcohol.

The personal care composition may contain, in addition to the liphophilic hydroxytyrosol carbonate ester compounds, from 0.001 wt. % to 20 wt. %, or at least 0.01 wt. %, or at least 0.1 wt. %, or at least 0.5 wt. %, or at least 1 wt. %, and up to 20 wt. %, or up to 15 wt. %, or up to 10 wt. %, or up to 8 wt. %, or up to 5 wt. % of a humectant, based on the weight of the personal care composition. Examples of suitable ranges include a personal care composition comprising, in addition to a liphophilic hydroxytyrosol carbonate ester compound, a humectant present in an amount of from 0.001 wt. % to 20 wt. %, or 0.001 wt. % to 15 wt. %, or 0.001 wt. % to 10 wt. %, or 0.001 wt. % to 8 wt. %, or 0.001 wt. % to 5 wt. %, or 0.01 wt. % to 20 wt. %, or 0.01 wt. % to 15 wt. %, or 0.01 wt. % to 10 wt. %, or 0.01 wt. % to 8 wt. %, or 0.01 wt. % to 5 wt. %, or 0.1 wt. % to 20 wt. %, or 0.1 wt. % to 15 wt. %, or 0.1 wt. % to 10 wt. %, or 0.1 wt. % to 8 wt. %, or 0.1 wt. % to 5 wt. %, or 0.5 wt. % to 20 wt. %, or 0.5 wt. % to 15 wt. %, or 0.5 wt. % to 10 wt. %, or 0.5 wt. % to 8 wt. %, or 0.5 wt. % to 5 wt. %, or 1 wt. % to 20 wt. %, or 1 wt. % to 15 wt. %, or 1 wt. % to 10 wt. %, or 1 wt. % to 8 wt. %, or 1 wt. % to 5 wt. %, in each case based on the weight of the personal care composition.

Exfoliants

The personal care composition of the invention can include liphophilic hydroxytyrosol carbonate ester compounds and an exfoliant. Examples of exfoliants include alpha-hydroxyacids and beta-hydroxyacids such as lactic acid, glycolic acid, salicylic acid; mak; acid, citric acid, and salts thereof, and fruit enzymes.

The personal care composition may contain, in addition to the liphophilic hydroxytyrosol carbonate ester compounds, from 0.001 wt. % to 20 wt. %, or at least 0.01 wt. %, or at least 0.1 wt. %, or at least 0.5 wt. %, or at least 1 wt. %, and up to 20 wt. %, or up to 15 wt. %, or up to 10 wt. %, or up to 8 wt. %, or up to 5 wt. % of an exfoliant, based on the weight of the personal care composition. Examples of suitable ranges include a personal care composition comprising, in addition to a liphophilic hydroxytyrosol carbonate ester compound, an exfoliant present in an amount of from 0.001 wt. % to 20 wt. %, or 0.001 wt. % to 15 wt. %, or 0.001 wt. % to 10 wt. %, or 0.001 wt. % to 8 wt. %, or 0.001 wt. % to 5 wt. %, or 0.01 wt. % to 20 wt. %, or 0.01 wt. % to 15 wt. %, or 0.01 wt. % to 10 wt. %, or 0.01 wt. % to 8 wt. %, or 0.01 wt. % to 5 wt. %, or 0.1 wt. % to 20 wt. %, or 0.1 wt. % to 15 wt. %, or 0.1 wt. % to 10 wt. %, or 0.1 wt. % to 8 wt. %, or 0.1 wt. % to 5 wt. %, or 0.5 wt. % to 20 wt. %, or 0.5 wt. % to 15 wt. %, or 0.5 wt. % to 10 wt. %, or 0.5 wt. % to 8 wt. %, or 0.5 wt. % to 5 wt. %, or 1 wt. % to 20 wt. %, or 1 wt. % to 15 wt. %, or 1 wt. % to 10 wt. %, or 1 wt. % to 8 wt. %, or 1 wt. % to 5 wt. %, in each case based on the weight of the personal care composition.

Water Proofing Agents

The personal care compositions of the invention can include liphophilic hydroxytyrosol carbonate ester compounds and a water proofing agent. Water proofing agents function to Examples of water proofing agents include magnesium/aluminum hydroxide stearate, copolymer of methyl vinyl ether/maleic anhydride, sulfopolyesters, sucrose acetate isobutyrate, calcium/sodium PVM/MA copolymer, polyvinylpyrrolidone, hydrogenated polyisobutene, hydrogenated rosinate, and acrylate copolymers, polyacrylamide, polyvinyl acetate, polyvinyl butyral, trimethylpropane triacrylate, VP/VA Copolymer, chitosan, and polyacrylates.

The personal care composition may contain, in addition to the liphophilic hydroxytyrosol carbonate ester compounds, from 0.001 wt. % to 20 wt. %, or at least 0.01 wt. %, or at least 0.1 wt. %, or at least 0.5 wt. %, or at least 1 wt. %, and up to 20 wt. %, or up to 15 wt. %, or up to 10 wt. %, or up to 8 wt. %, or up to 5 wt. % of a water proofing agent, based on the weight of the personal care composition. Examples of suitable ranges include a personal care composition comprising, in addition to a liphophilic hydroxytyrosol carbonate ester compound, a water proofing agent present in an amount of from 0.001 wt. % to 20 wt. %, or 0.001 wt. % to 15 wt. %, or 0.001 wt. % to 10 wt. %, or 0.001 wt. % to 8 wt. %, or 0.001 wt. % to 5 wt. %, or 0.01 wt. % to 20 wt. %, or 0.01 wt. % to 15 wt. %, or 0.01 wt. % to 10 wt. %, or 0.01 wt. % to 8 wt. %, or 0.01 wt. % to 5 wt. %, or 0.1 wt. % to 20 wt. %, or 0.1 wt. % to 15 wt. %, or 0.1 wt. % to 10 wt. %, or 0.1 wt. % to 8 wt. %, or 0.1 wt. % to 5 wt. %, or 0.1 wt. % to 5 wt. %, or 0.5 wt. % to 20 wt. %, or 0.5 wt. %, or 0.5 wt. % to 10 wt. %, or 0.5 wt. % to 8 wt. %, or 0.5 wt. % to 5 wt. %, or 1 wt. % to 20 wt. %, or 1 wt. % to 15 wt. %, or 1 wt. % to 10 wt. %, or 1 wt. % to 8 wt. %, or 1 wt. % to 5 wt. %, in each case based on the weight of the personal care composition.

Structuring Agents

The personal care composition of the invention can include liphophilic hydroxytyrosol carbonate ester compounds and structuring agents. Structuring agents stabilize a composition through its rheological characteristics, and can also function as an emulsifier or surfactant. Examples include carboxyvinyl polymer, carboxyvinyl polymer sodium salt, acrylic; acid/vinyl ester, pectin, algin, amphoteric acrylic polymers, sclerotium gum, hydroxyethyl cellulose, ethylene diaminiistearyl dirner dilinoleate copolymer, nylon, cellulose gum, sodium acrylates copolymer, polyvinylpyrollidone, agar, carboxymethyl cellulose, gum arabic, cylcopentasiloxane, dimethiconeivinyl dimethicone corsspolymer. polymeric sulfonic acid, lecithin, PEG-150 distearate, carbomer, bentonite, dextrin palmitate, stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about to about 5 ethylene oxide units, and mixtures thereof.

The personal care composition may contain, in addition to the liphophilic hydroxytyrosol carbonate ester compounds, from 0.001 wt. % to 20 wt. %, or at least 0.01 wt. %, or at least 0.1 wt. %, or at least 0.5 wt. %, or at least 1 wt. %, and up to 20 wt. %, or up to 15 wt. %, or up to 10 wt. %, or up to 8 wt. %, or up to 5 wt. % of a structuring agent, based on the weight of the personal care composition. Examples of suitable ranges include a personal care composition comprising, in addition to a liphophilic hydroxytyrosol carbonate ester compound, a structuring agent present in an amount of from 0.001 wt. % to 20 wt. %, or 0.001 wt. % to 15 wt. %, or 0.001 wt. % to 10 wt. %, or 0.001 wt. % to 8 wt. %, or 0.001 wt. % to 5 wt. %, or 0.01 wt. % to 20 wt. %, or 0.01 wt. % to 15 wt. %, or 0.01 wt. % to 10 wt. %, or 0.01 wt. % to 8 wt. %, or 0.01 wt. % to 5 wt. %, or 0.1 wt. % to 20 wt. %, or 0.1 wt. % to 15 wt. %, or 0.1 wt. % to 10 wt. %, or 0.1 wt. % to 8 wt. %, or 0.1 wt. % to 5 wt. %, or 0.5 wt. % to 20 wt. %, or 0.5 wt. % to 15 wt. %, or 0.5 wt. % to 10 wt. %, or 0.5 wt. % to 8 wt. %, or 0.5 wt. % to 5 wt. %, or 1 wt. % to 20 wt. %, or 1 wt. % to 15 wt. %, or 1 wt. % to 10 wt. %, or 1 wt. % to 8 wt. %, or 1 wt. % to 5 wt. %, in each case based on the weight of the personal care composition.

Gelling Agents

The personal care composition of the invention can include liphophilic hydroxytyrosol carbonate ester compounds and gelling agents. The gelling agent may be a polymeric; gelling agent or a mineral gelling agent. The gelling agent increases the viscosity of the personal care composition. Examples of gelling agents include polyethylene homopolymers and copolymers, polycaprolactones, styrenic block copolymers, pyrogenic silica, modified clays, partly or totally crosslinked elastomeric organopolysiloxanes of three-dimensional structure, galactomannans, and gums.

The polyethylene polymer may be polymerized with ethylene monomors and olefin comonomers other than ethylene. Examples of such olefinic copolymers include octenein weight ranges from 0.5 wt. % up to 50 wt. %, or up to 40 wt. %, or up to 30 wt. %, or up to 20 wt. %, or up to 15 wt. %, or up to 10 wt. %, based on the weight of the polyethylene copolymer.

The polycaprolactones can have a number average molecular weight ranging from 250 to 3000, or from 300 to 2500.

The polyethylene homopolymer or copolymer, or the polycaprolactone, may be present in the personal care composition in an amount ranging from 0.1 to 50% by weight, or from 0.1 to 35 wt. %, or from 0.5 to 25 wt. %, or from 1 to 20 wt %, or from 2 to 15 wt. %, based on the weight of the personal care composition.

Styrenic block copolymers are elastomers and amorphous. They can be made with styrene monomers and one, two, or three olefins having a single ethylenic unsaturation or poly-unsaturation. Examples of suitable co-monomers with styrene include ethylene, propylene, butadiene and isoprene. The styrenic block copolymer may be hydrogenated to reduce or eliminate unsaturation. Examples of styrenic block copolymers include those made from the monomors with a block structure of: styrene-ethylene/propylene-styrene copolymers; styrene-ethylene/butadiene-styrene copolymers, styrene-isoprene-styrene copolymers and styrene-butadiene-styrene copolymers. These copolymers are sold under the tradename of Kraton, such as Kraton™ G1650E, Kraton™ G1652, Kraton™ D1101, Kraton™ D1102 and Kraton™ D1160 by Kraton.

The personal care composition may contain styrenic block copolymer in an amount ranging from at least 0.05 wt. %, or at least 0.1 wt. %, and up to 10 wt. or up to 5 wt. %, or up to 3 wt. %, or up to 2 wt. %, based on the weight of the personal care composition.

The personal care composition may contain pyrogenic silica as a gelling agent, optionally hydrophobically treated on its surface, with a particle size of less than 10 microns.

The personal care composition may contain modified clays as a gelling agent. Examples of modified clays include hectorites modified with a $C_{10}$-$C_{22}$ fatty acid ammonium salts, such as hectorite modified with distearyldimethylammonium chloride and mixtures thereof.

The personal care composition may contain partially or totally crosslinked elastomeric organopolysiloxanes of three-dimensional structure as a gelling agent. Examples include those sold under the name KSG6, KSG16 and KSG18 by Shin-Etsu, Trefil E-505C and Trefil E-506C by Dow Corning, Gransil SR-CYC, SR DMF10, SR-DC556, SR 5CYC gel, SR DMF 10 gel and SR DC 556 gel by Grant Industries, and SF 1204 and JK 113 by General Electric.

The personal care composition may contain galactomannans having from 1 to 6 hydroxyl groups per monosaccharide unit. Examples include guar gum alkylated with $C_1$-$C_6$ alkyl chains, such as the ethylated guar having a degree of substitution of from 2 to 3, such as that sold by Aqualon under the name N-Hance-AG. Other suitable gums include silicone gums, such as PDMS gums, having a viscosity of more than 100 000 cSt.

Emulsifiers

The personal care composition of the invention can include liphophilic hydroxytyrosol carbonate ester compounds and emulsifiers. Emulsifiers reduce the interfacial tension between phases and improve the formulation and stability of an emulsion. The emulsifiers can be nonionic, cationic, anionic, and zwitterionic emulsifiers. Examples include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, PPG-2 methyl glucose ether distearate, ceteth-10, poiysorbate 80, cetyl phosphate, potassium cetyl phosphate, diethanolamine cetyl phosphate, polysorbate 60, glyceryl stearate, PEG-100 stearate, and combinations thereof.

The personal care composition may contain, in addition to the liphophilic hydroxytyrosol carbonate ester compounds, from 0.001 wt. % to 20 wt. %, or at least 0.01 wt. %, or at least 0.1 wt. %, or at least 0.5 wt. %, or at least 1 wt. %, and up to 20 wt. %, or up to 15 wt. %, or up to 10 wt. %, or up to 8 wt. %, or up to 5 wt. % of an emulsifier, based on the weight of the personal care composition. Examples of suitable ranges include a personal care composition comprising, in addition to a liphophilic hydroxytyrosol carbonate ester compound, an emulsifier present in an amount of from 0.001 wt. % to 20 wt. %, or 0.001 wt. % to 15 wt. %, or 0.001 wt. % to 10 wt. %, or 0.001 wt. % to 8 wt. %, or 0.001 wt. % to 5 wt. %, or 0.01 wt. % to 20 wt. %, or 0.01 wt. % to 15 wt. %, or 0.01 wt. % to 10 wt. %, or 0.01 wt. % to 8 wt. %, or 0.01 wt. % to 5 wt. %, or 0.1 wt. % to 20 wt. %, or 0.1 wt. % to 15 wt. %, or 0.1 wt. % to 10 wt. %, or 0.1 wt. % to 8 wt. %, or 0.1 wt. % to 5 wt. %, or 0.5 wt. % to 20 wt. %, or 0.5 wt. % to 15 wt. %, or 0.5 wt. % to 10 wt. %, or 0.5 wt. % to 8 wt. %, or 0.5 wt. % to 5 wt. %, or 1 wt. % to 20 wt. %, or 1 wt. % to 15 wt. %, or 1 wt. % to 10 wt. %, or 1 wt. % to 8 wt. %, or 1 wt. % to 5 wt. %, in each case based on the weight of the personal care composition.

The liphophilic hydroxytyrosol carbonate ester compounds contained in the personal care compositions have the capability of reducing the appearance of fine lines or wrinkles, or reducing age spots. The skin condition can be dry skin, aged, saggy, with fine lines or wrinkles, or with age spots (liver spots, sun spots, discolored spots, hyper-pigmentation, etc). The personal care compositions can be applied to the skin, including skin in the decollete region (e.g., neck, shoulders, andlor upper chest), facial skin, and other parts of the body, including arms, hands, chest, abdomen, upper and lower back, legs, buttocks, feet, etc.

The form of the personal care composition can be varied. The personal care composition of the invention may be presented in the form of a cast product. Examples of cast products include sticks, crayons, in a dish which can be used by direct contact or with a sponge, which find applications as a cast foundation, cast blusher or cast eyeshadow, lipstick, a care base or care balm for the lips or a concealer product. They may also be presented in the form of a soft paste, a gel, a cream, a lotion, a liquid, a wax, an aerosol, a polish, a powder, etc.

The personal care compositions of the invention can be pourable at 25° C.

The personal care compositions of the invention can be anhydrous, meaning that the composition contains 5 wt. % or less, or 4 wt. % or less, or 3.5 wt. % or less, or 3 wt. % or less, or 2 wt. % or less water. Examples of anhydrous personal care composition include tanning oils and moisturizing compounds (e.g. petrolatum).

The personal care compositions of the invention are desirably dermatologically acceptable.

The personal care compositions of the invention can be an emulsion, a paste, or a colloidal dispersion. The colloid, or the dispersed phase particles, may have an average particle size ranging from 1 nm to 1000 nm, or 5 nm to 500 nm, or 10 nm to 100 nm. The personal care composition may comprise a colloidal dispersion in which the disperse phase is present in an amount ranging from 0.5 to less than 50 wt. %, or from 2 to 40 wt. %, or form 2 to 30 wt. %, based on the weight of the composition. The colloidal suspension can be a solid disperse phase in a liquid or solid continuous phase, or a liquid disperse phase in a liquid or solid continuous phase.

The novel processes, compounds, and compositions provided by the present invention are further illustrated by the following examples.

EXAMPLES

Example 1

4-Hydroxyphenethyl Palmitate (Compound 4, $R_2$=n-$C_{15}H_{31}$)

Palmic acid (192 g, 0.75 mole) was melted at 66° C. Tyrosol (103.5 g. 0.75 moles) along with 11 g of Novozyme 435 were added and the thick slurry was stirred gently overnight at 60-65° C. with a slow sweep of nitrogen to carry out the water. Analysis by tic indicated a complete reaction. Heptane (600 mL) was added in order to separate the enzyme beads from the product, which was done by filtration through a 2 micron glass filter. The heptane solution was cooled to 45°

C. and seeded. The slurry was allowed to cool slowly to room temperature overnight and then was further cooled to 0-5° C. After stirring for 1 hr, it was filtered and washed with cold heptane and the product was dried to give 246.3 g (87%) of white material, mp 58-59° C. The H$^1$ NMR spectrum was consistent with the structure.

Example 2

3-Formyl-4-Hydroxyphenethyl Palmitate (Compound 5, $R_2$=n-$C_{15}H_{31}$)

The ester from Example 1 (25.9 g, 68.6 mmole) was dissolved in 125 mL of THF under nitrogen. No precautions for presence of water, other than using a fresh bottle of HPLC grade THF, were taken. Anhydrous Magnesium Chloride (12.2 g, 128 mmoles) and 26.9 g (266 mmoles) of triethylamine were then added and the slurry was warmed to 40° C. The slurry thickened while it was being heated. Paraformaldehyde (13.5 g, 450 mmoles) was then added and the slurry was held at 40-45° C. for 23 hr. Analysis by HPLC (230 nm) indicated an incomplete reaction, with about 11% starting material and 2% of the corresponding 2-hydroxyethyl intermediate. The slurry was cooled and a solution of 25 mL of conc HCl in 75 mL water was added, holding the temperature below 25° C. Then 200 mL of water was added to the solution at which point the product precipitated. The slurry was filtered and air-dried to give 25.5 g (92%) of the product whose composition was the same as the advance analysis. The material was purified by recrystallization from 175 mL of isopropyl alcohol (filtration and washing at 0-5° C.) to give 16 g (63% recovery) of material with an HPLC assay of 95.5%; mp 53-55° C., H$^1$ NMR was consistent with the structure.

Example 3

3,4-Dihydroxyphenethyl Palmitate (Compound 6, $R_2$=n-$C_{15}H_{31}$)

The aldehyde from example 2 (23.6 g, 58.5 mmole mmole) was dissolved in 100 mL of isopropyl alcohol at 45° C. The solution was cooled to 35° C. and 8.8 g of 45% KOH (70 mmoles) in 150 mL of water was dripped in at 30-35° C. The solution was cooled 20-25° C. and a solution of 8 g of 35% hydrogen peroxide (82 mmole) in 10 mL of water was dripped in over about 20 min at 20-25° C. A mild exotherm was noted, but the temperature was easily held by a water bath. The product precipitated during the addition of the peroxide. The slurry was held 1 hr at which time it exhibited a weak peroxide test (starch-iodide paper). Acetic acid (2mL) was added to reduce the pH from ca. 8 to ca. 6. The slurry was filtered, washed with water, and the product was air-dried to give 20.8 g (91%) of white solid. HPLC analysis indicated an area % product of 93.6, the melting point was 61-62° C., and the H$^1$ NMR was consistent with the structure. The composition of Example 3 prior to isolation by HPLC: 91% product, 1% formate ester 9, 3% starting material.

Example 4

3,4-Bis(ethoxycarbonyloxy)phenethyl palmitate Compound 2, $R_2$=n-$C_{15}H_{31}$, $R_1$=$C_2H_5$ The diol from Example 3 (51.2 g, 0.13 mole) was dissolved in 600 mL of acetone under nitrogen. Ethylchloroformate (26.4 mL, 0.27 mole) was then added in a stream at 25-30° C. The solution was cooled to 0-5° C. while purging with a sweep of nitrogen. The nitrogen sweep was replaced with a nitrogen blanket and 28 g (0.277 mole) of triethylamine was added slowly (Strong Exotherm) at −2° to 5° C. After the addition the resulting slurry was allowed to warm to 20° C. over about 1 hr and was drowned into 2800 mL water. The resulting oil was stirred overnight at which point it partially solidified. It was extracted into ethyl acetate and the resulting solution was back washed with water. After drying (MgSO$_4$) the ethyl acetate was removed with vacuum and the resulting solid (64.9 g) was recrystallized from 300 mL of ethanol, seeding at 15° C. and filtering and washing at 0-5° C. The white solid obtained (54.4 g, 78%) had an HPLC assay (210 nm) of 93.7% and a mp of 39-40° C. Another recrystallization from 300 mL of ethanol raised the HPLC assay to 96.4% (85% recovery). The H$^1$ NMR spectrum confirmed the structure.

Comparative Example 5

Compound of Example 2 Reacted Using the Meta-Chloroperbenzoic Acid Route Described in Piersanti et al, *Tetrahedron Lett,* 52, 4938-4940, 2011.

3.13 g of the aldehyde from Example 2 (7.7 mmoles), 50 mL of dichloromethane, and 2.46 g of 77% meta-chloroperbenzoic acid (11 mmoles) were stirred overnight. Analysis by HPLC (by-product 3-chlorobenzoic acid was not detected by the HPLC method) indicated about 20% of unreacted aldehyde, 32% of the desired product, and about 20% of a formate ester corresponding to the structure 9 below. The remaining peaks were not identified. Another 0.5 g of meta-chloroperbenzoic acid was added and the reaction was refluxed overnight, but the HPLC was not much improved. After work-up by the referenced procedure the HPLC area percent of desired product was 61% and the area percent of starting material was 17%. Some of the corresponding ortho-quinone of the structure 10 and some of the formate ester 9 were also observed, but it was not possible to accurately integrate these peaks. The composition did not precipitate. Given the low assay of the desired product as detected by HPLC, the composition was discarded.

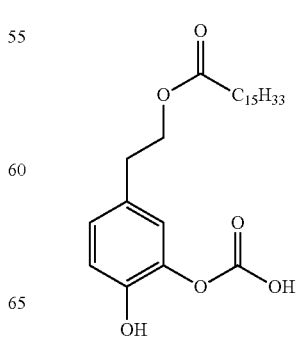

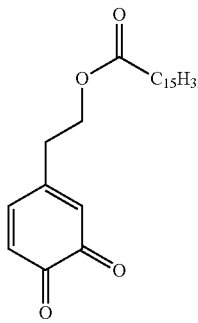

Example 6

Enzymatic Hydrolysis of 3,4-Bis(ethoxyoarbonyloxy)phenethyl palmitate Compound 2, $R_2$=n-$C_{15}H_{31}$, $R_1$'$C_2H_5$ 3,4-Bis(ethoxycarbonyloxy)phenethyl palmitate (100 mg; 0.186 mmol) was dissolved in 2 mL of toluene. Novozyme 435 (*Candida antarctica* lipase B immobilized on an acrylic resin) (100 mg) was added followed by 2 mL of pH 7 phosphate buffer. The mixture was stirred vigorously and periodically analyzed by HPLC. After 24 h, LC analysis indicated 75.4% conversion of Compound 2 to hydroxytyrosol. After 48 h, LC analysis indicated 82.6% conversion of Compound 2 to hydroxytyrosol.

A control reaction without enzyme showed no conversion to hydroxytyrosol.

Comparative Example 7

Hydroxytyrosol Trihexanoate

Hydroxytyrosol (1 g; 6.49 mmol) was dissolved in 2.3 mL (2.25 g; 28.4 mmol; 4.4 equiv) and toluene (9 mL) was added to afford a cloudy solution. The mixture was cooled in ice-water and hexanoyl chloride (2.88 g; 21.4 mmol; 3.3 equiv) was added. Solic formed upon the addition and stirring became difficult, so the mixture was diluted with 5 mL of toluene to allow stirring. The mixture was stirred for 45 min in ice-water at which point LC analysis indicated no hydroxytyrosol and one major peak. The mixture was diluted with ethyl acetate and washed sequentially with water, 1.5 M HCl (20 mL), and 5% sodium bicarbonate (20 mL). The resulting organic solution was dried with magnesium sulfate, filtered, and concentrated. The resulting crude product was filtered through a pad of silica gel and eluted with 1:4 ethyl acetate:heptane, and the filtrate was stripped under high vacuum to afford 2.09 g (72%) of hydroxytyrosol trihexanoate. The $H^1$ NMR spectrum confirmed the structure.

Comparative Example 8

Enzymatic Hydrolysis of Hydroxytyrosol Trihexanoate

Hydroxytyrosol trihexanoate from Comparative Example 8 (100 mg; 0.223 mmol) was dissolved in 2 mL of toluene. Novozyme 435 (*Candida antarctica* lipase B immobilized on an acrylic resin)(100 mg) was added followed by 2 mL of pH 7 phosphate buffer. The mixture was stirred vigorously and periodically analyzed by HPLC. After 24 h, LC analysis indicated <1% conversion of hydroxytyrosol trihexanoate to hydroxytyrosol. After 48 h, LC analysis indicated <1% conversion of hydroxytyrosol trihexanoate to hydroxytyrosol.

TABLE 1

Comparative enzymatic hydrolysis of hydroxytyrosol ester dicarbonate and hydroxytyrosol triester.

| | Compound | |
|---|---|---|
| | 3,4-Bis(ethoxycarbonyloxy)phenethyl palmitate | Hydroxytyrosol trihexanoate |
| Example | Example 6 | Comparative Example 8 |
| | Enzymatic conversion to hydroxytyrosol | |
| 24 h | 75.4% | <1% |
| 48 h | 82.6% | <1% |

What we claim is:

1. A lipophilic hydroxytyrosol carbonate ester compound having a structure represented by the general Formula 2:

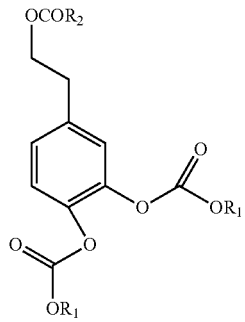

wherein $R_1$ is a saturated or unsaturated, branched or straight chain, substituted or unsubstituted, aliphatic, alicyclic, or alkaryl $C_1$-$C_{22}$ aliphatic, alicyclic, or alkaryl group; and wherein $R_2$ is a saturated or unsaturated, branched or straight chain, substituted or unsubstituted $C_2$-$C_{24}$ aliphatic, alicyclic, or alkaryl group.

2. The compound of claim 1, wherein $R_2$ is a $C_8$-$C_{24}$ group.

3. The compound of claim 2, wherein $R_2$ is a $C_{10}$-$C_{24}$ group.

4. The compound of claim 3, wherein $R_2$ is a $C_{12}$-$C_{24}$ group.

5. The compound of claim 4, wherein $R_2$ has at least 6 more carbon atoms than the $R_1$ group.

6. The compound of claim 4, wherein $R_2$ has at least 10 more carbon atoms than the $R_1$ group.

7. The compound of claim 1, wherein $R_1$ is substituted with one to three groups selected from $C_1$-$C_6$-alkoxy, carboxyl, $C_1$-$C_{15}$ aminocarbonyl, $C_1$-$C_{15}$ amido, cyano, $C_2$-$C_{15}$-alkoxycarbonyl, $C_2$-$C_{15}$-alkoxycarbonyloxy, $C_2$-$C_{15}$ alkanoyloxy, hydroxy, aryl, substituted aryl, heteroaryl, substituted heteroaryl, thiol, thioether, and halogen.

8. The compound of any one of claims 1-7, wherein $R_2$ is an aliphatic group.

9. The compound of any one of claims 1-7, wherein $R_2$ is un-substituted.

10. The compound of any one of claims 1-7, wherein $R_2$=$C_{12}$-$C_{24}$ and $R_1$=$C_1$-$C_6$.

11. A composition for topical application to a keratinous surface, said composition comprising a lipophilic hydroxytyrosol carbonate ester compound of the general Formula 2:

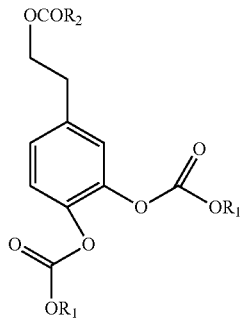

wherein $R_1$ is a saturated or unsaturated, branched or straight chain, substituted or unsubstituted, aliphatic, alicyclic, or alkaryl $C_1$-$C_{22}$ aliphatic, alicyclic, or alkaryl group; and wherein $R_2$ is a saturated or unsaturated, branched or straight chain, substituted or un-substituted $C_2$-$C_{24}$ aliphatic, alicyclic, or alkaryl group.

12. The composition of claim 11, wherein said composition comprises a cosmetic composition.

13. The composition of claim 12, wherein said composition comprises an eyeliner, eyeshadow, lipstick, mascara, foundation, blush, or nail polish.

14. The composition of claim 11, wherein said composition comprises a skin care composition.

15. The composition of claim 14, wherein said composition comprises a skin moisturizer, anti-aging lotion, infant care product, body oil, after-bath and shower product, soap, shampoo, or sun screen or sun tan lotion.

* * * * *